(12) United States Patent
Heilman et al.

(10) Patent No.: US 12,090,291 B2
(45) Date of Patent: *Sep. 17, 2024

(54) ENDOVASCULAR CEREBROSPINAL FLUID SHUNT

(71) Applicant: Tufts Medical Center, Inc., Boston, MA (US)

(72) Inventors: Carl Heilman, Wayland, MA (US); Adel M. Malek, Weston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 305 days.

This patent is subject to a terminal disclaimer.

(21) Appl. No.: 17/666,039

(22) Filed: Feb. 7, 2022

(65) Prior Publication Data

US 2022/0288363 A1 Sep. 15, 2022

Related U.S. Application Data

(63) Continuation of application No. 16/444,982, filed on Jun. 18, 2019, now Pat. No. 11,278,708, which is a
(Continued)

(51) Int. Cl.
*A61M 27/00* (2006.01)
*A61B 17/12* (2006.01)
(Continued)

(52) U.S. Cl.
CPC ........... *A61M 27/006* (2013.01); *A61B 90/39* (2016.02); *A61B 17/12168* (2013.01);
(Continued)

(58) Field of Classification Search
CPC .............. A61M 27/006; A61M 25/04; A61M 2210/0693; A61M 2210/12;
(Continued)

(56) References Cited

U.S. PATENT DOCUMENTS 575,997 A 1/1897 Spencer
3,298,372 A 1/1967 Feinberg
(Continued)

FOREIGN PATENT DOCUMENTS

CN 1895694 A 1/2007
EP 0964636 A1 12/1999
(Continued)

OTHER PUBLICATIONS

Oh et al., "Implantable Microdevice for the Treatment of Hydrocephalus," Drexel University, Mar. 2011, 155 pages.
(Continued)

*Primary Examiner* — Adam Marcetich
(74) *Attorney, Agent, or Firm* — Occhiuti & Rohlicek LLP

(57) ABSTRACT

Implantable shunt devices and methods for draining cerebrospinal fluid from a patient's subarachnoid space include a shunt having opposed first and second ends, the second end being constructed to penetrate a wall of a sigmoid, transverse, straight, or sagittal sinus of the patient, a one-way valve, a hollow passageway extending between the second end and the one-way valve such that cerebrospinal fluid can be drained through the second end and out through the valve, and a mechanism coupled to the shunt and configured to anchor the shunt at a desired location proximal to the subarachnoid space.

20 Claims, 23 Drawing Sheets

Related U.S. Application Data continuation of application No. 15/480,543, filed on Apr. 6, 2017, now Pat. No. 10,596,357, which is a continuation of application No. 14/596,335, filed on Jan. 14, 2015, now Pat. No. 9,737,696, which is a continuation of application No. 14/259,614, filed on Apr. 23, 2014, now abandoned.

(60) Provisional application No. 61/927,558, filed on Jan. 15, 2014.

(51) Int. Cl.
| | | |
|---|---|---|
| *A61B 90/00* | (2016.01) | |
| *A61F 2/86* | (2013.01) | |
| *A61F 2/88* | (2006.01) | |
| *A61F 2/90* | (2013.01) | |
| *A61F 2/91* | (2013.01) | |
| *A61M 25/04* | (2006.01) | |

(52) U.S. Cl.
CPC . *A61B 17/12172* (2013.01); *A61B 2090/3966* (2016.02); *A61F 2/86* (2013.01); *A61F 2/88* (2013.01); *A61F 2/90* (2013.01); *A61F 2/91* (2013.01); *A61M 25/04* (2013.01); *A61M 2210/0693* (2013.01); *A61M 2210/12* (2013.01)

(58) Field of Classification Search
CPC ........ A61B 17/12168; A61B 17/12172; A61B 2090/3966; A61F 2/86; A61F 2/90
See application file for complete search history.

(56) References Cited

U.S. PATENT DOCUMENTS

| | | |
|---|---|---|
| 3,492,996 A | 2/1970 | Fountain |
| 3,894,541 A | 7/1975 | El-Shafei |
| 4,413,985 A | 11/1983 | Wellner et al. |
| 4,474,569 A | 10/1984 | Newkirk |
| 4,475,898 A | 10/1984 | Brodner et al. |
| 4,631,051 A | 12/1986 | Harris |
| 4,737,153 A | 4/1988 | Shimamura et al. |
| 4,950,232 A | 8/1990 | Ruzicka et al. |
| 5,000,731 A | 3/1991 | Wong et al. |
| 5,122,114 A | 6/1992 | Miller et al. |
| 5,137,288 A | 8/1992 | Starkey et al. |
| 5,160,325 A | 11/1992 | Nichols et al. |
| 5,193,546 A | 3/1993 | Shaknovich |
| 5,221,261 A | 6/1993 | Termin et al. |
| 5,385,541 A | 1/1995 | Kirsch et al. |
| 5,405,316 A | 4/1995 | Magram |
| 5,429,144 A | 7/1995 | Wilk |
| 5,496,329 A | 3/1996 | Reisinger |
| 5,508,824 A | 4/1996 | Baba |
| 5,551,427 A | 9/1996 | Altman |
| 5,562,641 A | 10/1996 | Flomenblit et al. |
| 5,634,475 A | 6/1997 | Wolvek |
| 5,725,571 A | 3/1998 | Imbert et al. |
| 5,725,572 A | 3/1998 | Lam et al. |
| 5,746,725 A | 5/1998 | Shalon et al. |
| 5,755,775 A | 5/1998 | Trerotola et al. |
| 5,792,157 A | 8/1998 | Mische et al. |
| 5,800,520 A | 9/1998 | Fogarty et al. |
| 5,830,222 A | 11/1998 | Makower |
| 5,851,199 A | 12/1998 | Peerless et al. |
| 5,885,258 A | 3/1999 | Sachdeva et al. |
| 5,976,131 A | 11/1999 | Guglielmi et al. |
| 5,984,929 A | 11/1999 | Bashiri et al. |
| 6,015,405 A | 1/2000 | Schwartz et al. |
| 6,066,158 A | 5/2000 | Engelson et al. |
| 6,068,638 A | 5/2000 | Makower |
| 6,071,292 A | 6/2000 | Makower et al. |
| 6,093,199 A | 7/2000 | Brown et al. |
| 6,096,053 A | 8/2000 | Bates |
| 6,126,628 A | 10/2000 | Nissels |
| 6,126,649 A | 10/2000 | VanTassel et al. |
| 6,126,672 A | 10/2000 | Berryman et al. |
| 6,159,225 A | 12/2000 | Makower |
| 6,186,972 B1 | 2/2001 | Nelson et al. |
| 6,190,353 B1 | 2/2001 | Makower et al. |
| 6,228,088 B1 | 5/2001 | Miller et al. |
| 6,231,587 B1 | 5/2001 | Makower |
| 6,248,112 B1 | 6/2001 | Gambale et al. |
| 6,264,625 B1 | 7/2001 | Rubenstein et al. |
| 6,283,934 B1 | 9/2001 | Børgesen |
| 6,283,947 B1 | 9/2001 | Mirzaee |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,350,271 B1 | 2/2002 | Kurz et al. |
| 6,375,615 B1 | 4/2002 | Flaherty et al. |
| 6,379,319 B1 | 4/2002 | Garibotto et al. |
| 6,402,771 B1 | 6/2002 | Palmer et al. |
| 6,425,909 B1 | 7/2002 | Dieck et al. |
| 6,432,127 B1 | 8/2002 | Kim et al. |
| 6,464,709 B2 | 10/2002 | Shennib et al. |
| 6,491,707 B2 | 12/2002 | Makower et al. |
| 6,508,824 B1 | 1/2003 | Flaherty et al. |
| 6,527,790 B2 | 3/2003 | Chien et al. |
| 6,530,935 B2 | 3/2003 | Wensel et al. |
| 6,544,230 B1 | 4/2003 | Flaherty et al. |
| 6,561,998 B1 | 5/2003 | Roth et al. |
| 6,569,145 B1 | 5/2003 | Shmulewitz et al. |
| 6,575,997 B1 | 6/2003 | Palmer et al. |
| 6,579,302 B2 | 6/2003 | Duerig et al. |
| 6,579,311 B1 | 6/2003 | Makower |
| 6,589,164 B1 | 7/2003 | Flaherty |
| 6,602,241 B2 | 8/2003 | Makower et al. |
| 6,613,081 B2 | 9/2003 | Kim et al. |
| 6,616,675 B1 | 9/2003 | Evard et al. |
| 6,638,293 B1 | 10/2003 | Makower et al. |
| 6,655,386 B1 | 12/2003 | Makower et al. |
| 6,660,021 B1 | 12/2003 | Palmer et al. |
| 6,660,024 B1 | 12/2003 | Flaherty et al. |
| 6,663,650 B2 | 12/2003 | Sepetka et al. |
| 6,685,648 B2 | 2/2004 | Flaherty et al. |
| 6,685,716 B1 | 2/2004 | Flaherty et al. |
| 6,709,444 B1 | 3/2004 | Makower |
| 6,716,238 B2 | 4/2004 | Elliott |
| 6,719,750 B2 | 4/2004 | Varner et al. |
| 6,726,677 B1 | 4/2004 | Flaherty et al. |
| 6,730,104 B1 | 5/2004 | Sepetka et al. |
| 6,740,112 B2 | 5/2004 | Yodfat et al. |
| 6,746,426 B1 | 6/2004 | Flaherty et al. |
| 6,746,464 B1 | 6/2004 | Makower |
| 6,776,795 B2 | 8/2004 | Pelton |
| 6,863,684 B2 | 3/2005 | Kim et al. |
| 6,960,217 B2 | 11/2005 | Bolduc |
| 7,037,288 B2 | 5/2006 | Rosenberg et al. |
| 7,056,325 B1 | 6/2006 | Makower et al. |
| 7,083,588 B1 | 8/2006 | Shmulewitz et al. |
| 7,094,230 B2 | 8/2006 | Flaherty et al. |
| 7,118,549 B2 | 10/2006 | Chan |
| 7,134,438 B2 | 11/2006 | Makower et al. |
| 7,135,009 B2 | 11/2006 | Tu et al. |
| 7,141,041 B2 | 11/2006 | Seward |
| 7,150,737 B2 | 12/2006 | Purdy et al. |
| 7,172,571 B2 | 2/2007 | Moskowitz et al. |
| 7,179,270 B2 | 2/2007 | Makower |
| 7,189,221 B2 | 3/2007 | Silverberg et al. |
| 7,191,015 B2 | 3/2007 | Lamson et al. |
| 7,286,879 B2 | 10/2007 | Wallace |
| 7,300,458 B2 | 11/2007 | Henkes et al. |
| 7,303,571 B2 | 12/2007 | Makower et al. |
| 7,316,655 B2 | 1/2008 | Garibotto et al. |
| 7,316,692 B2 | 1/2008 | Huffmaster |
| 7,351,247 B2 | 4/2008 | Kupiecki et al. |
| 7,354,416 B2 | 4/2008 | Quiroz-Mercado et al. |
| 7,357,794 B2 | 4/2008 | Makower et al. |
| 7,361,168 B2 | 4/2008 | Makower et al. |
| 7,407,506 B2 | 8/2008 | Makower |

(56) References Cited

U.S. PATENT DOCUMENTS

| | | |
|---|---|---|
| 7,476,211 B2 | 1/2009 | Nilsson |
| 7,513,883 B2 | 4/2009 | Glenn |
| 7,524,512 B2 | 4/2009 | Di Bartolomeo |
| 7,547,294 B2 | 6/2009 | Seward et al. |
| 7,559,923 B2 | 7/2009 | Seward et al. |
| 7,606,615 B2 | 10/2009 | Makower et al. |
| 7,608,064 B2 | 10/2009 | Putz |
| 7,621,928 B2 | 11/2009 | Thramann et al. |
| 7,621,950 B1 | 11/2009 | Globerman et al. |
| 7,637,870 B2 | 12/2009 | Flaherty et al. |
| 7,648,517 B2 | 1/2010 | Makower et al. |
| 7,657,325 B2 | 2/2010 | Williams |
| 7,670,329 B2 | 3/2010 | Flaherty et al. |
| 7,691,077 B2 | 4/2010 | Kralick et al. |
| 7,691,080 B2 | 4/2010 | Seward et al. |
| 7,708,711 B2 | 5/2010 | Tu et al. |
| 7,715,896 B2 | 5/2010 | Ramzipoor et al. |
| 7,729,738 B2 | 6/2010 | Flaherty et al. |
| 7,797,053 B2 | 9/2010 | Atkinson et al. |
| 7,846,172 B2 | 12/2010 | Makower |
| 7,947,062 B2 | 5/2011 | Chin et al. |
| 7,955,343 B2 | 6/2011 | Makower et al. |
| 7,966,057 B2 | 6/2011 | Macaulay et al. |
| 7,989,042 B2 | 8/2011 | Obara et al. |
| 7,998,103 B2 | 8/2011 | El Shafei et al. |
| 8,012,115 B2 | 9/2011 | Karageozian |
| 8,043,247 B1 | 10/2011 | Glenn |
| 8,070,694 B2 | 12/2011 | Galdonik et al. |
| 8,075,580 B2 | 12/2011 | Makower |
| 8,083,708 B2 | 12/2011 | Flaherty et al. |
| 8,088,140 B2 | 1/2012 | Ferrera et al. |
| 8,090,430 B2 | 1/2012 | Makower et al. |
| 8,118,827 B2 | 2/2012 | Duerig et al. |
| 8,214,015 B2 | 7/2012 | Macaulay et al. |
| 8,292,950 B2 | 10/2012 | Dorn et al. |
| 8,295,947 B2 | 10/2012 | Lamson et al. |
| 8,317,748 B2 | 11/2012 | Fiorella et al. |
| 8,323,305 B2 | 12/2012 | Epstein et al. |
| 8,366,651 B2 | 2/2013 | Dakin et al. |
| 8,376,979 B2 | 2/2013 | Kapadia |
| 8,486,104 B2 | 7/2013 | Samson et al. |
| 8,540,759 B2 | 9/2013 | Porter |
| 8,585,596 B1 | 11/2013 | Flaherty et al. |
| 8,672,871 B2 | 3/2014 | Heilman et al. |
| 8,672,920 B2 | 3/2014 | Makower et al. |
| 8,672,964 B2 | 3/2014 | Inderbitzi |
| 8,715,314 B1 | 5/2014 | Janardhan et al. |
| 8,727,988 B2 | 5/2014 | Flaherty et al. |
| 8,740,833 B2 | 6/2014 | Moskowitz et al. |
| 8,753,366 B2 | 6/2014 | Makower et al. |
| 8,795,317 B2 | 8/2014 | Grandfield et al. |
| 8,827,944 B2 | 9/2014 | Sevrain |
| 8,852,205 B2 | 10/2014 | Brady et al. |
| 8,876,792 B2 | 11/2014 | Holmin et al. |
| 8,926,680 B2 | 1/2015 | Ferrera et al. |
| 8,945,142 B2 | 2/2015 | Schaeffer et al. |
| 8,961,452 B2 | 2/2015 | Purdy |
| 8,974,513 B2 | 3/2015 | Ford et al. |
| 8,979,801 B2 | 3/2015 | Lamson et al. |
| 8,992,456 B1 | 3/2015 | Powell |
| 9,023,059 B2 | 5/2015 | Loushin et al. |
| 9,039,749 B2 | 5/2015 | Shrivastava et al. |
| 9,113,936 B2 | 8/2015 | Palmer et al. |
| 9,119,656 B2 | 9/2015 | Bose et al. |
| 9,168,172 B1 | 10/2015 | Berdahl |
| 9,199,067 B2 | 12/2015 | Heilman et al. |
| 9,314,600 B2 | 4/2016 | Paris et al. |
| 9,345,858 B2 | 5/2016 | Flaherty et al. |
| 9,351,772 B2 | 5/2016 | Mische |
| 9,387,311 B1 | 7/2016 | Heilman et al. |
| 9,387,331 B2 | 7/2016 | Zhao et al. |
| 9,402,982 B2 | 8/2016 | Baert et al. |
| 9,433,429 B2 | 9/2016 | Vale et al. |
| 9,545,505 B2 | 1/2017 | Heilman et al. |
| 9,549,284 B2 | 1/2017 | Ji et al. |
| 9,597,230 B2 | 3/2017 | Haffner et al. |
| 9,669,195 B2 | 6/2017 | Heilman et al. |
| 9,675,786 B2 | 6/2017 | Stone et al. |
| 9,682,216 B2 | 6/2017 | Teitelbaum |
| 9,713,483 B2 | 7/2017 | Makower et al. |
| 9,724,501 B2 | 8/2017 | Heilman et al. |
| 9,737,696 B2 | 8/2017 | Heilman et al. |
| 10,004,621 B2 | 6/2018 | Kelly |
| 10,022,251 B2 | 7/2018 | Teitelbaum |
| 10,058,686 B2 | 8/2018 | Heilman et al. |
| 10,272,230 B2 | 4/2019 | Malek et al. |
| 10,279,154 B2 | 5/2019 | Heilman et al. |
| 10,307,576 B2 | 6/2019 | Heilman et al. |
| 10,307,577 B2 | 6/2019 | Malek et al. |
| 10,625,061 B2 | 4/2020 | Borgesen |
| 2001/0025643 A1 | 10/2001 | Foley |
| 2001/0041899 A1 | 11/2001 | Foster |
| 2002/0123786 A1 | 9/2002 | Gittings et al. |
| 2002/0183786 A1 | 12/2002 | Girton |
| 2002/0188308 A1 | 12/2002 | Tu et al. |
| 2003/0040754 A1 | 2/2003 | Mitchell et al. |
| 2003/0135147 A1 | 7/2003 | Rosenberg et al. |
| 2003/0181938 A1 | 9/2003 | Roth et al. |
| 2003/0187495 A1 | 10/2003 | Cully et al. |
| 2003/0191520 A1 | 10/2003 | Pelton |
| 2003/0220604 A1 | 11/2003 | Al-Anazi |
| 2003/0225395 A1 | 12/2003 | Griffis et al. |
| 2003/0229366 A1 | 12/2003 | Reggie et al. |
| 2004/0059280 A1 | 3/2004 | Makower et al. |
| 2004/0073242 A1 | 4/2004 | Chanduszko |
| 2004/0087887 A1 | 5/2004 | Nilsson |
| 2004/0147871 A1 | 7/2004 | Burnett |
| 2004/0153110 A1 | 8/2004 | Kurz et al. |
| 2004/0176743 A1 | 9/2004 | Morris et al. |
| 2004/0186368 A1 | 9/2004 | Ramzipoor et al. |
| 2004/0236309 A1 | 11/2004 | Yang |
| 2004/0236409 A1 | 11/2004 | Pelton et al. |
| 2004/0249439 A1 | 12/2004 | Richter et al. |
| 2004/0254517 A1 | 12/2004 | Quiroz-Mercado et al. |
| 2004/0260384 A1 | 12/2004 | Allen |
| 2005/0033334 A1 | 2/2005 | Santra et al. |
| 2005/0119668 A1 | 6/2005 | Teague et al. |
| 2005/0137646 A1 | 6/2005 | Wallace et al. |
| 2005/0234509 A1 | 10/2005 | Widomski et al. |
| 2005/0245906 A1 | 11/2005 | Makower et al. |
| 2005/0251151 A1 | 11/2005 | Teague |
| 2005/0256510 A1 | 11/2005 | Moskowitz et al. |
| 2005/0281863 A1 | 12/2005 | Anderson et al. |
| 2006/0004368 A1 | 1/2006 | Zaleski et al. |
| 2006/0015089 A1 | 1/2006 | Meglin et al. |
| 2006/0015152 A1 | 1/2006 | Wallace |
| 2006/0079915 A1 | 4/2006 | Chin et al. |
| 2006/0089704 A1 | 4/2006 | Douglas |
| 2006/0173440 A1 | 8/2006 | Lamson et al. |
| 2006/0217755 A1 | 9/2006 | Eversull et al. |
| 2006/0224101 A1 | 10/2006 | Glenn |
| 2006/0241687 A1 | 10/2006 | Glaser et al. |
| 2006/0259063 A1 | 11/2006 | Bates et al. |
| 2006/0276738 A1 | 12/2006 | Becker |
| 2007/0005125 A1 | 1/2007 | Berenstein et al. |
| 2007/0073337 A1 | 3/2007 | Abbott et al. |
| 2007/0112291 A1 | 5/2007 | Borgesen |
| 2007/0129746 A1 | 6/2007 | Mische |
| 2007/0156230 A1 | 7/2007 | Dugan et al. |
| 2007/0179426 A1 | 8/2007 | Selden |
| 2007/0179428 A1 | 8/2007 | Kralick, et al. |
| 2007/0208376 A1 | 9/2007 | Meng |
| 2007/0225794 A1 | 9/2007 | Thramann et al. |
| 2007/0276316 A1 | 11/2007 | Haffner et al. |
| 2008/0045863 A1 | 2/2008 | Bakos |
| 2008/0057106 A1 | 3/2008 | Erickson et al. |
| 2008/0058759 A1 | 3/2008 | Makower et al. |
| 2008/0097398 A1 | 4/2008 | Mitelberg et al. |
| 2008/0125805 A1 | 5/2008 | Mische |
| 2008/0249458 A1 | 10/2008 | Yamasaki |
| 2009/0005645 A1 | 1/2009 | Frassica et al. |
| 2009/0017098 A1 | 1/2009 | Di Bartolomeo |
| 2009/0069828 A1 | 3/2009 | Martin et al. |
| 2009/0076357 A1 | 3/2009 | Purdy |

(56) References Cited

U.S. PATENT DOCUMENTS

| | | |
|---|---|---|
| 2009/0171293 A1 | 7/2009 | Yang et al. |
| 2009/0287291 A1 | 11/2009 | Becking et al. |
| 2009/0318903 A1* | 12/2009 | Shachar ............ A61M 5/16827 |
| | | 604/891.1 |
| 2010/0010476 A1 | 1/2010 | Galdonik et al. |
| 2010/0016887 A1 | 1/2010 | Inderbitzi |
| 2010/0063531 A1 | 3/2010 | Rudakov et al. |
| 2010/0076404 A1 | 3/2010 | Ring |
| 2010/0121357 A1 | 5/2010 | Flaherty et al. |
| 2010/0191168 A1 | 7/2010 | Heilman |
| 2010/0222732 A1 | 9/2010 | Sevrain |
| 2011/0082385 A1 | 4/2011 | Diaz et al. |
| 2011/0319917 A1 | 12/2011 | Ferrera et al. |
| 2012/0109111 A1 | 5/2012 | Li |
| 2012/0130467 A1 | 5/2012 | Selden et al. |
| 2012/0130468 A1 | 5/2012 | Khosravi et al. |
| 2012/0172844 A1 | 7/2012 | Mullen |
| 2013/0035628 A1 | 2/2013 | Garrison et al. |
| 2013/0144328 A1 | 6/2013 | Weber et al. |
| 2013/0178828 A1 | 7/2013 | Takagi et al. |
| 2014/0005586 A1 | 1/2014 | Feinstein |
| 2014/0052047 A1 | 2/2014 | Wilson |
| 2014/0052160 A1 | 2/2014 | Singh et al. |
| 2014/0128905 A1 | 5/2014 | Molaei |
| 2014/0180098 A1 | 6/2014 | Flaherty et al. |
| 2014/0180222 A1 | 6/2014 | Flaherty et al. |
| 2014/0207044 A1 | 7/2014 | Baert et al. |
| 2014/0236207 A1 | 8/2014 | Makower et al. |
| 2014/0276342 A1 | 9/2014 | Stone et al. |
| 2014/0277079 A1 | 9/2014 | Vale et al. |
| 2014/0288414 A1 | 9/2014 | Makower et al. |
| 2014/0336559 A1 | 11/2014 | Heilman et al. |
| 2015/0196741 A1 | 7/2015 | Heilman et al. |
| 2015/0201303 A1 | 7/2015 | Ji et al. |
| 2015/0209058 A1 | 7/2015 | Ferrera et al. |
| 2015/0223908 A1 | 8/2015 | Westerfeld et al. |
| 2015/0258260 A1 | 9/2015 | Tuseth |
| 2015/0305756 A1 | 10/2015 | Rosenbluth et al. |
| 2016/0136398 A1 | 5/2016 | Heilman et al. |
| 2016/0143756 A1 | 5/2016 | Rezac et al. |
| 2016/0151056 A1 | 6/2016 | Lederman et al. |
| 2016/0287276 A1 | 10/2016 | Cox et al. |
| 2017/0050000 A1 | 2/2017 | Randall |
| 2018/0015267 A1 | 1/2018 | Heilman et al. |
| 2018/0126132 A1 | 5/2018 | Heilman et al. |
| 2019/0021750 A1 | 1/2019 | Heilman et al. |

FOREIGN PATENT DOCUMENTS

| | | |
|---|---|---|
| EP | 1047341 A1 | 11/2000 |
| EP | 1067869 A2 | 1/2001 |
| EP | 1067874 A1 | 1/2001 |
| EP | 1082070 A1 | 3/2001 |
| EP | 1171183 A1 | 1/2002 |
| EP | 1253859 A1 | 11/2002 |
| EP | 1359967 A2 | 11/2003 |
| EP | 1377335 A2 | 1/2004 |
| EP | 1491232 A2 | 12/2004 |
| EP | 1496956 A2 | 1/2005 |
| EP | 1854499 A1 | 11/2007 |
| EP | 1981413 A2 | 10/2008 |
| EP | 2589344 A1 | 5/2013 |
| GB | 2089215 A | 6/1982 |
| JP | 2006289086 A | 10/2006 |
| WO | 19980016161 A1 | 4/1998 |
| WO | 20020022028 A2 | 3/2002 |
| WO | 20060080113 A1 | 8/2006 |
| WO | 2007115314 A2 | 10/2007 |
| WO | 20090014723 A1 | 1/2009 |
| WO | 20090036039 A1 | 3/2009 |
| WO | 20090088783 A2 | 7/2009 |
| WO | 20090126935 A2 | 10/2009 |
| WO | 20110011787 A2 | 1/2011 |
| WO | 2012009518 A1 | 1/2012 |
| WO | 2012158152 A1 | 11/2012 |
| WO | 20130034602 A1 | 3/2013 |
| WO | 2014165754 A1 | 10/2014 |
| WO | 20150108917 A1 | 7/2015 |
| WO | 2016070147 A1 | 5/2016 |
| WO | 201707554 A2 | 1/2017 |
| WO | 2017075544 A1 | 5/2017 |
| WO | 2017117427 A1 | 7/2017 |
| WO | 2018005621 A1 | 1/2018 |
| WO | 2018071600 A1 | 4/2018 |
| WO | 2018160966 A1 | 9/2018 |

OTHER PUBLICATIONS

Toma et al., "Ventriculosinus Shunt", Neurosurg Review, dated Feb. 23, 2010, 7 pages.
Weiner et al., "Current Treatment of Normal-Pressure Hydrocephalus: Comparison of Flow-Regulated and Differential-Pressure Shunt Valves", Neurosurgery vol. 37(5), dated Nov. 1995, 13 pages.
White, Ian, et al. "Prepontine Shunting for Pseudotumor Cerebri in Previously Failed Shunt Patients: A 5-Year Analysis." Neurosurgery, vol. 88, No. 2, Oct. 10, 2020, pp. 306-312., https://doi.org/10.1093/neuros/nyaa417.

* cited by examiner

Anterior to Posterior View of Right Sigmoid Venous Sinus

ENDOVASCULAR CEREBROSPINAL FLUID SHUNT

CROSS-REFERENCE TO RELATED APPLICATION

This application is a continuation of U.S. application Ser. No. 16/444,982, filed Jun. 18, 2019, which is a continuation of U.S. application Ser. No. 15/480,543 filed on Apr. 6, 2017, which is a continuation of U.S. application Ser. No. 14/596,335 filed on Jan. 14, 2015, which is a continuation of U.S. application Ser. No. 14/259,614 filed on Apr. 23, 2014, which claims priority to U.S. Provisional Application No. 61/927,558 filed on Jan. 15, 2014, the contents of which are hereby incorporated by reference in their entirety.

TECHNICAL FIELD

The present disclosure relates to shunts capable of draining cerebrospinal fluid to the venous system.

BACKGROUND

It is known to treat hydrocephalus by draining cerebrospinal fluid (CSF) from the brain with a drain tube, catheter or shunt. See U.S. Pat. Nos. 5,385,541 and 4,950,232. These known devices are complex and invasive. The risk for infection is also increased due to the complexity of these devices.

The known shunts are limited to areas of placement due to fluid flow control; however, fluid flow still poses difficulties due to the complexity of the devices and the placement areas. Commonly, the shunts/catheters are placed through the skull of the patient. This placement requires an open surgical procedure performed under general anesthesia. The shunts/catheters also require pressure control to facilitate CSF flow. Moreover, the known shunts and methods of placements do not work in conjunction with a body's natural disease control processes.

Thus, there is a need for an endovascular shunt that can be inserted into the venous system percutaneously, without the need for open surgery and concomitant risk of infection.

SUMMARY

The present disclosure relates to endovascular CSF shunts that drain CSF from the subarachnoid space around the cerebellum into a dural venous sinus. As used in the present disclosure, the phrase "dural venous sinus" and other references to the term "sinus" mean the sigmoid sinus, transverse sinus, straight sinus, or sagittal sinus.

The present disclosure also relates to methods of draining CSF by inserting, and deploying, and optionally detaching, one or more of the shunts disclosed herein by an endovascular route through the venous system. For example, the venous system may be accessed either through the femoral vein or the jugular vein percutaneously.

The endovascular cerebrospinal fluid shunt devices as described herein are an improvement over the standard cerebrospinal fluid shunts, because they can be placed into a patient percutaneously via a catheter inserted into the venous system of the body through a needle hole, without the need for open surgery and the skin incisions required with current shunt devices. In some patients, the shunt devices can be inserted without general anesthesia, which is not possible with current cerebrospinal fluid shunts. The shunt devices also will allow for more physiologic drainage of cerebrospinal fluid since the device is shunting cerebrospinal fluid into the same cerebral venous system that occurs naturally in people without impaired CSF drainage.

One aspect of the present disclosure is to provide implantable shunt devices for draining fluid from a patient's subarachnoid space. The devices include a shunt having opposed first and second ends. The devices also include a one-way valve and a tip configured to penetrate the sinus "wall" (e.g., a wall of dura) to access the subarachnoid space. In some embodiments, a one-way valve is located at the first end of the shunt and a helical tip is disposed at the second end. In use, the helical tip penetrates the sigmoid sinus wall of the patient and a hollow passageway extending between the helical tip and the first end allows the CSF to be drained through the helical tip and out through the valve.

Another aspect of the present disclosure provides methods for draining cerebrospinal fluid from a patient's subarachnoid space. The methods include providing a shunt having opposed first and second ends, delivering the shunt to the sinus wall, implanting the helical tip in the sinus wall of the patient; and draining cerebrospinal fluid from the patient.

In another general aspect, implantable shunt devices for draining cerebrospinal fluid from a patient's subarachnoid space include a shunt having opposed first and second ends, the second end being constructed to penetrate a wall of a sinus of the patient, a one-way valve disposed at either end or between the ends of the shunt, a hollow passageway extending the length of the shunt such that cerebrospinal fluid can be drained through the second end, valve, and first end into the sinus lumen. The shunt device can also include a mechanism coupled to the shunt and configured to anchor the shunt at a desired location proximal to the subarachnoid space.

Aspects may include one or more of the following features in various combinations as indicated in the appended claims.

The shunt device may be sized and configured to be positioned within the sigmoid sinus, transverse sinus, straight sinus, or sagittal sinus. The shunt device can include a stent device configured for insertion into the sinus of the patient. The stent device can include a helical coil. The helical coil can be self-expanding. The stent device can include a self-expanding basket. The stent device can include a circumferential mesh. The circumferential mesh can be self-expanding. The stent device can include a plurality of individual coils coupled to a connecting member. Each coil of the plurality of coils can be self-expanding.

The shunt device can include a helical tip configured to be positioned within the subarachnoid space. The shunt device can include a coiled cannula with a three-dimensional shape, wherein the coiled cannula is configured to be positioned within the subarachnoid space. The coiled cannula can be configured to realize its three-dimensional shape upon being positioned within the subarachnoid space. The shunt device can include an umbrella shaped screen configured to be positioned within the subarachnoid space. The umbrella shaped screen can be configured to realize its umbrella shape upon being positioned within the subarachnoid space. The shunt device can include a globe shaped screen configured to be positioned within the subarachnoid space. The globe shaped screen can be configured to realize its globe shape upon being positioned within the subarachnoid space.

Aspects may include one or more of the following advantages.

Among other advantages, the portions of the endovascular cerebrospinal fluid shunt (eCSFS) devices that are specifically designed be placed into the cerebral spinal fluid (CSF)

space (e.g., the subarachnoid space) can be shielded from the surrounding brain parenchyma (e.g., the cerebellum) by a shielding mechanism, e.g., a stent-like or umbrella-type device, advantageously enabling the continuous flow of cerebral spinal fluid through the device. That is, certain embodiments described herein include shielding mechanisms that reduce or mitigate the potential occlusion of openings in eCSFS devices that are designed to enable the passage of CSF through the device by structurally separating, e.g., pushing back, the brain parenchyma from the subarachnoid portions of the eCSFS device. Additionally, these shielding mechanisms can also create and maintain a space for CSF to pool within the subarachnoid space. Maintaining a well-defined space for CSF to pool around the subarachnoid portion of the eCSFS device ensures that CSF will flow to the venous system and enables the shunt device to operatively maintain normal intracranial pressure by draining excess CSF from the subarachnoid space.

The use of stents in conjunction with or as a part of the shunt devices described herein results in a better anchoring of eCSFS devices in their desired locations. The use of stents can also simplify the process of delivering and implanting eCSFS devices.

Use of a radiopaque material to form a ring or other marker for a stent mounted port provides the advantage that the stent mounted port can be easily located using fluoroscopy techniques.

Use of a specialized catheterization apparatus including two or more stabilization balloons permits passage of blood around the balloon and through the sigmoid sinus, transverse sinus, straight sinus, or sagittal sinus during implantation of an eCSFS device. Since blood is permitted to flow around the stabilization balloons, venous drainage of the cerebral tissue continues during implantation of the eCSFS device.

These and other features, aspects, and advantages of the present disclosure will become more apparent from the following detailed description relative to the accompanied drawings, in which:

DETAILED DESCRIPTION

1 Endovascular Shunt Device

Figure 1:
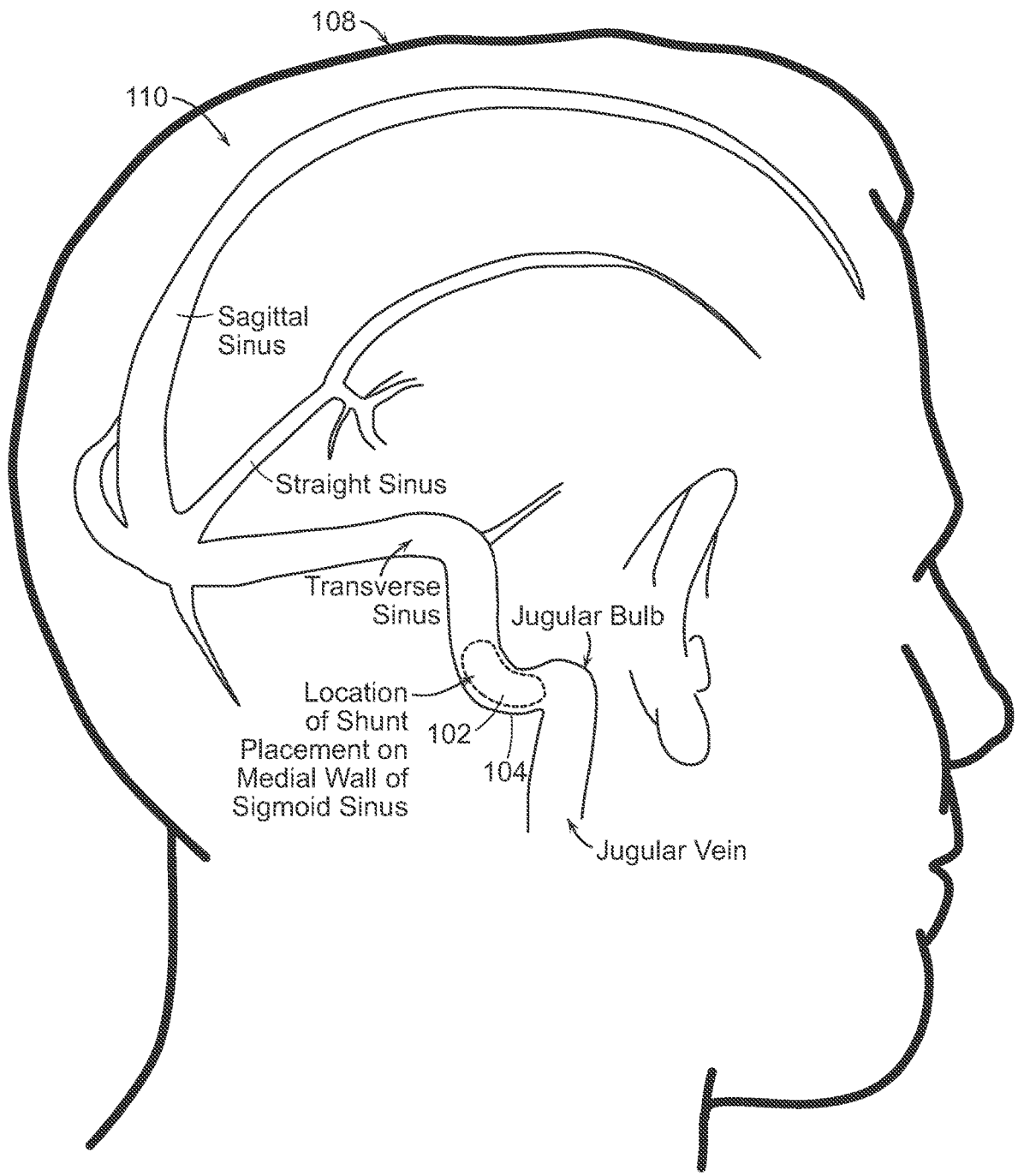
FIG. 1 is a schematic of an anatomy of the venous system in the skull of a human.

Referring to FIG. 1, a first view of a patient's head illustrates that the endovascular shunt devices and stents described herein can be delivered to a preferred location 102 of placement in the medial wall of the sigmoid sinus 104 of the venous system 110 of a patient 108. Alternatively, the shunt devices and stents described herein can be delivered to the other large diameter dural venous sinuses disclosed herein: the transverse sinus, straight sinus, or sagittal sinus shown in FIG. 1.

Figure 2:
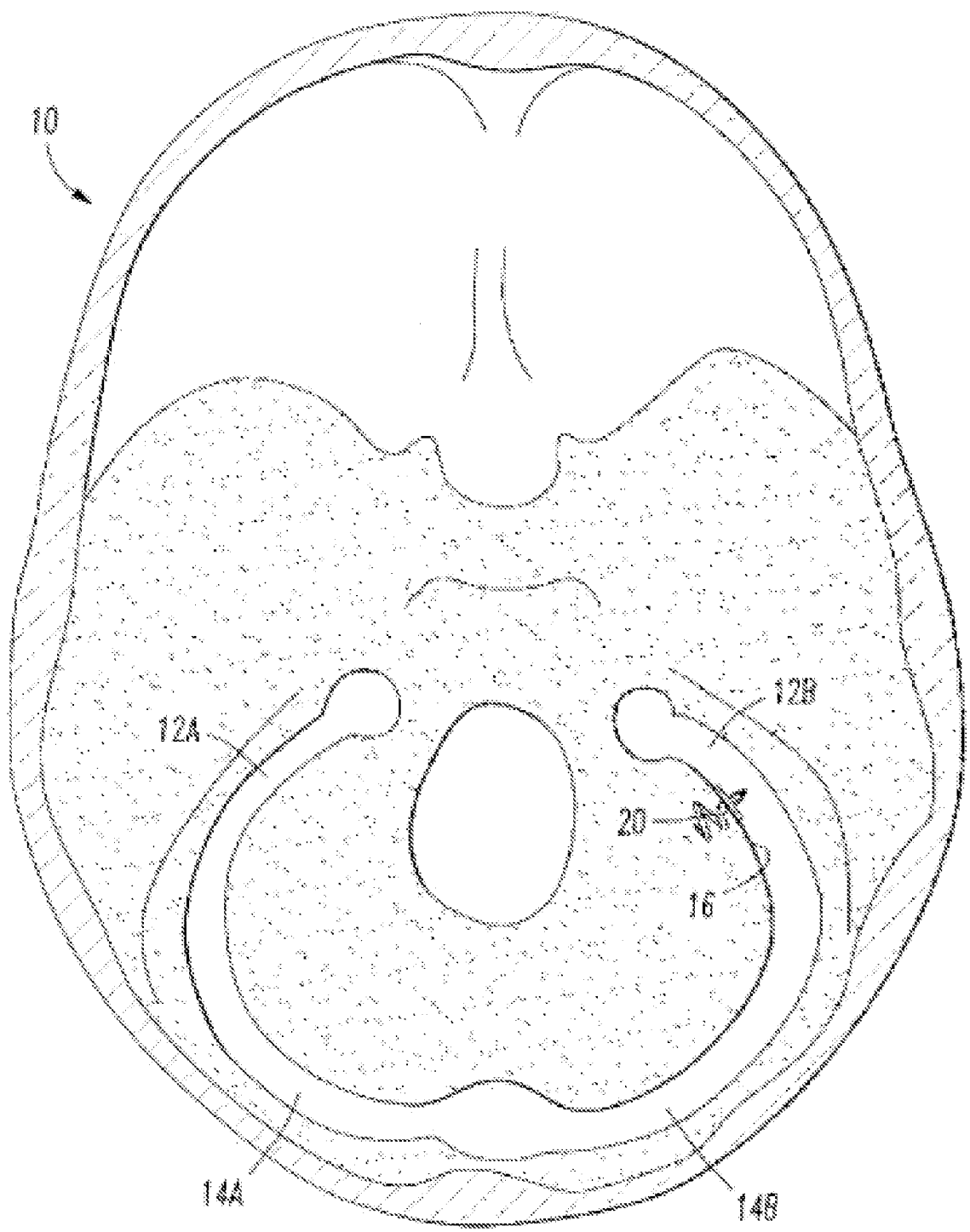
FIG. 2 is a schematic of a top view of a human skull base with the brain removed illustrating the placement of an endovascular shunt penetrating the sigmoid sinus wall into the subarachnoid space.

Referring to FIG. 2, a second view of the patients head illustrates that in general, the endovascular shunt devices can be delivered to the right or left sigmoid sinus 12A, 12B of a patient's skull 10 via either the right or left jugular vein, respectively, of the venous system. The sigmoid sinus lumen 12 is located between the temporal bone (FIGS. 4-6) and the cerebellum.

A shunt 20 is implanted into a sigmoid sinus wall 16, so that one end communicates with CSF located in the cistern or CSF space 18 around the cerebellum 19. The device of the present disclosure uses the body's natural disease control mechanisms by delivering the CSF from cistern 18 into sigmoid sinus lumen 12 of the venous system. The venous system of the patient can be accessed either through the femoral or jugular veins (not shown) percutaneously. It should be appreciated that the shunt device of the present disclosure can be delivered to the sigmoid sinus via other veins.

Figure 3:
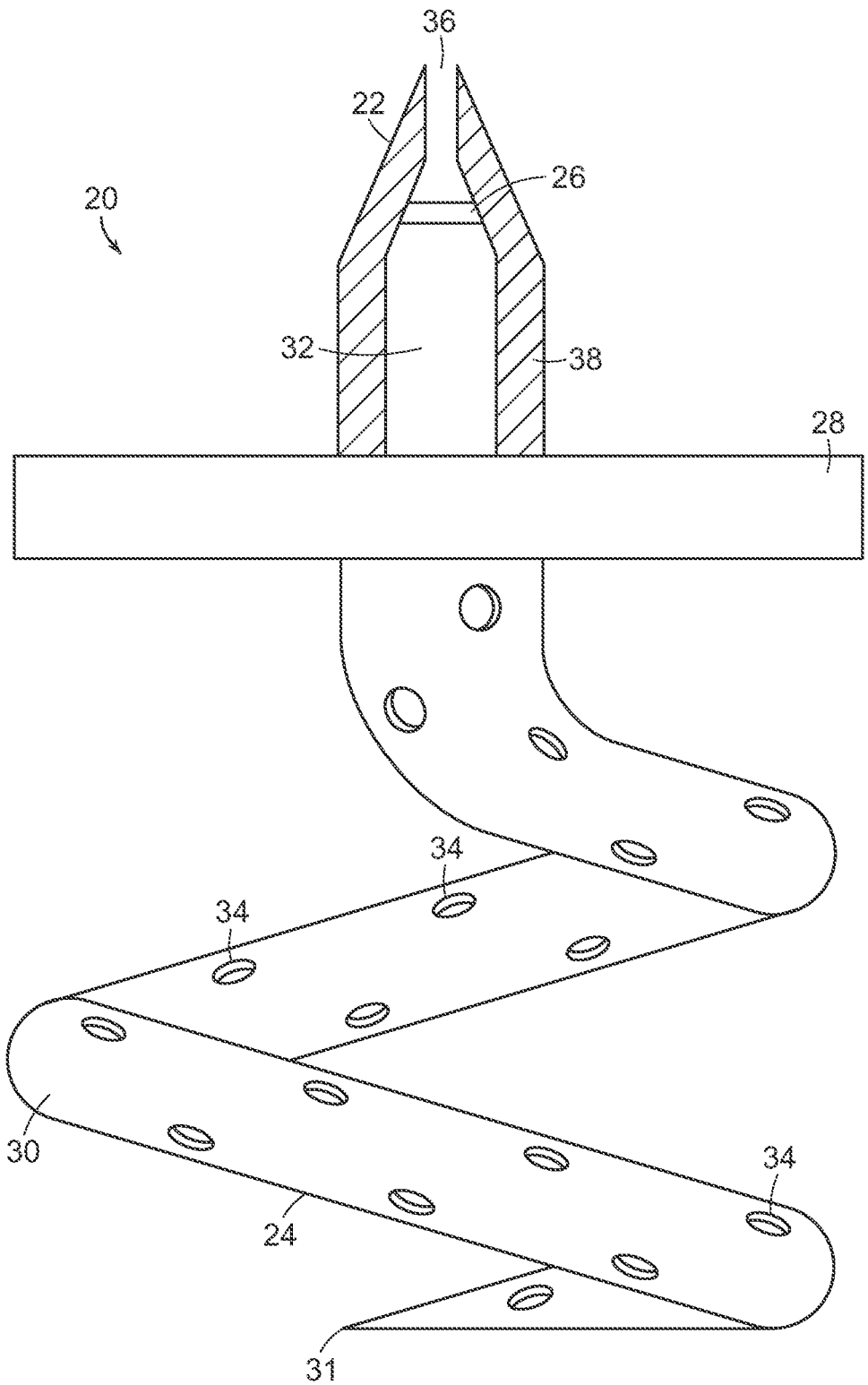
FIG. 3 is a partial cross-section of an embodiment of the endovascular shunt of FIG. 2.

As shown in FIG. 3, one embodiment of the endovascular CSF shunt 20 of the present disclosure includes opposed first and second ends 22, 24. A one-way valve 26 is located at first end 22. As will be described further herein, CSF can travel through shunt 20 and out end 22, however, other fluid (e.g., blood) cannot enter the shunt from open end 22.

A helical tip 30 is located at second end 24. As will be described further herein, helical tip 30 has a closed sharpened end 31 that is adapted to penetrate sinus wall 16. Tip 30 includes a plurality of apertures 34 through which the CSF enters the tip. A hollow passageway 32 extends from tip 30 and open end 22, such that the CSF fluid entering through apertures 34 can pass through valve 26 and pass from an outlet 36.

Figure 4:
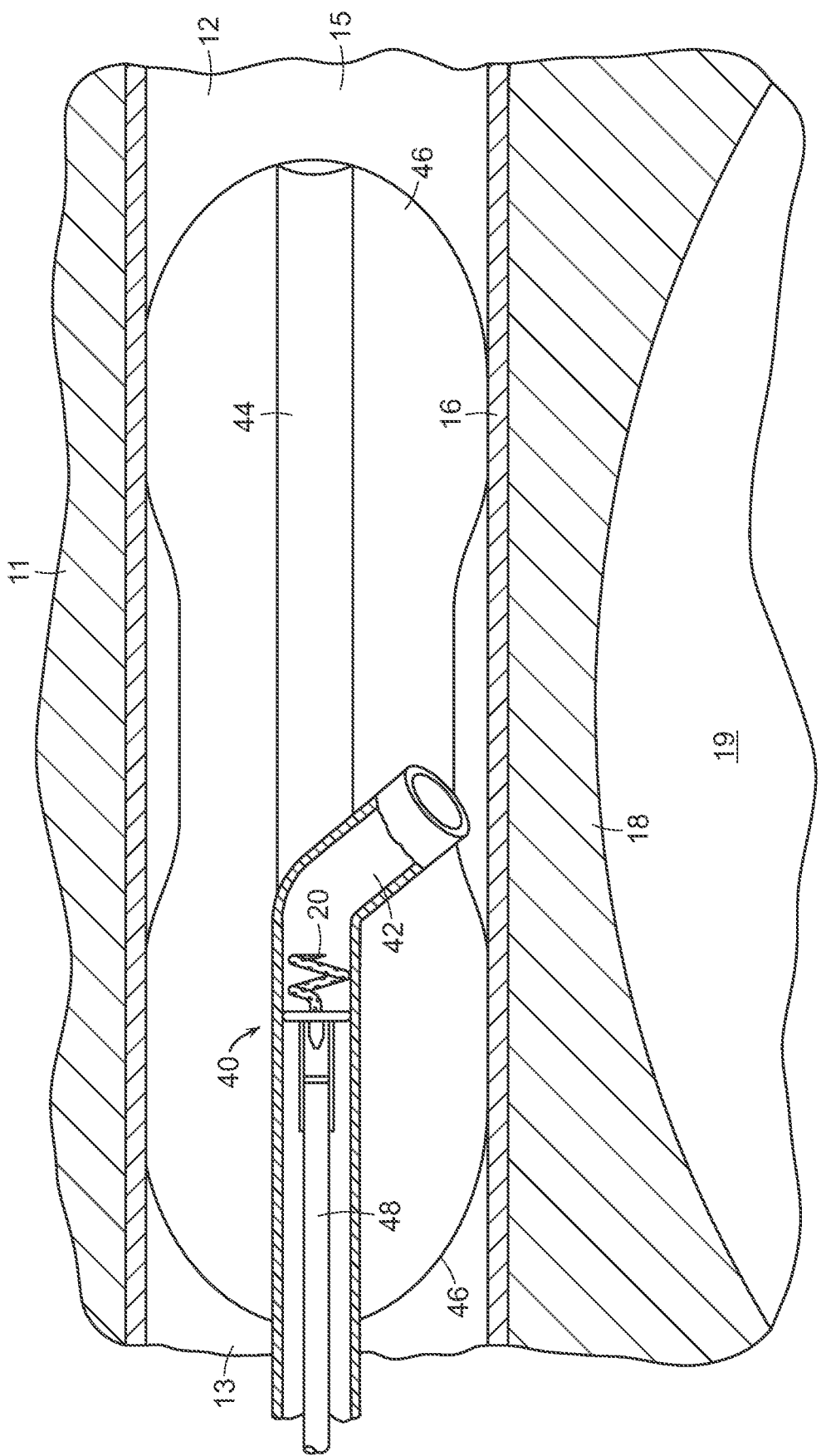
FIG. 4 illustrates the delivery of the endovascular shunt of FIG. 3 to the CSF space of a patient's venous system.
Figure 5:
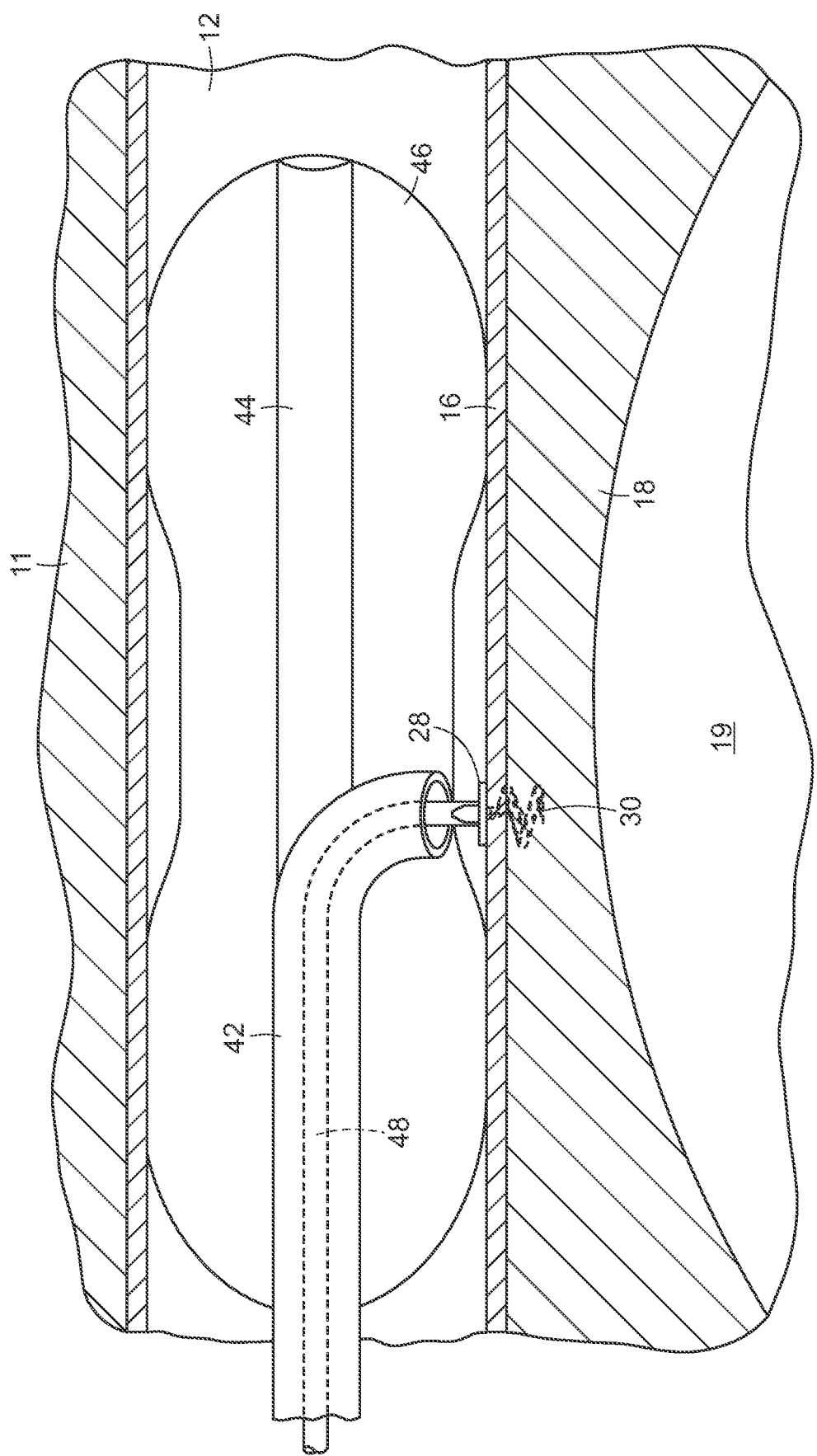
FIG. 5 illustrates the implantation of the endovascular shunt of FIG. 3 into the sigmoid sinus wall.
Figure 6:
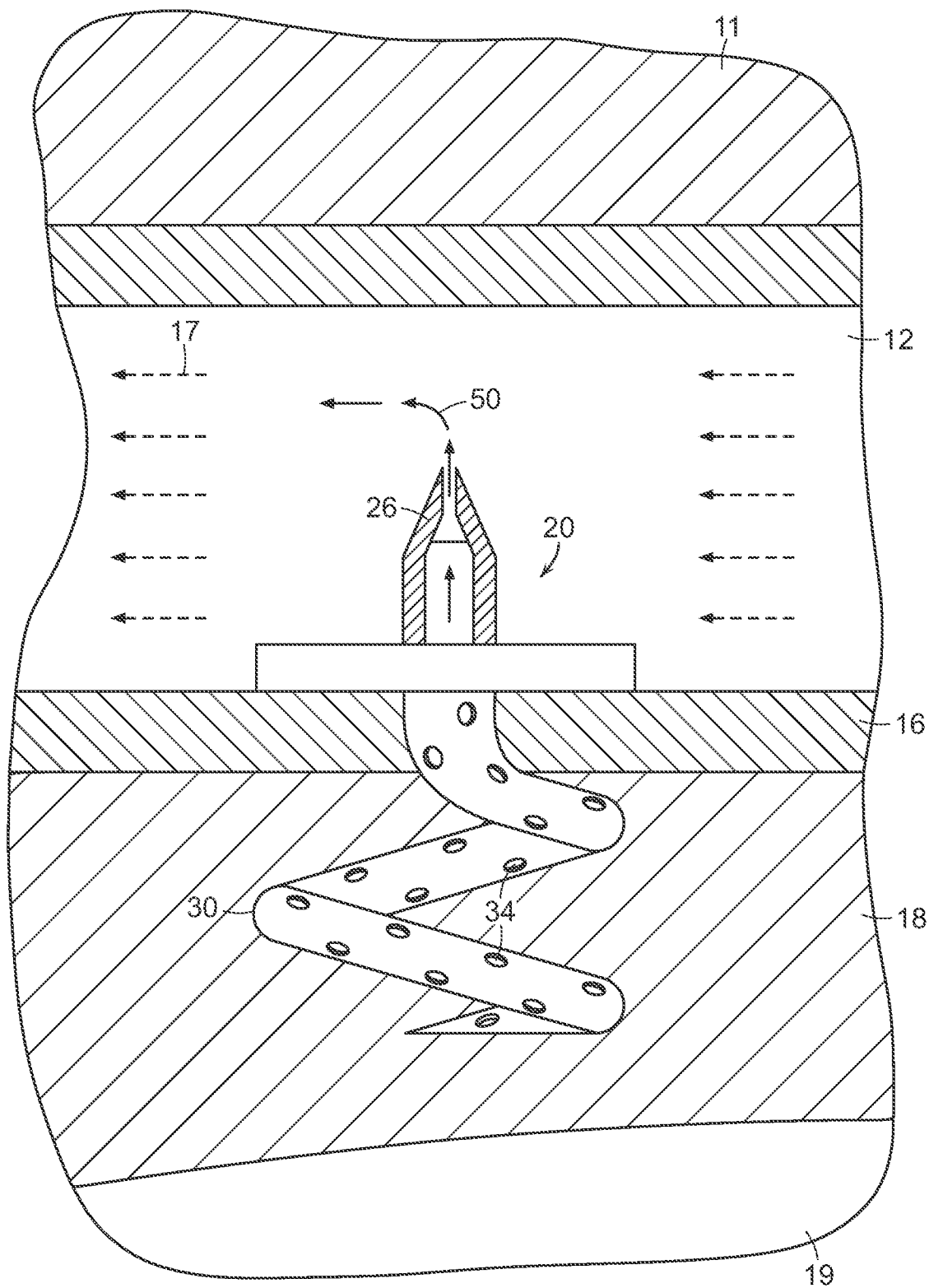
FIG. 6 illustrates the endovascular shunt of FIG. 3 implanted in the sigmoid sinus wall.

Referring to FIGS. 4-6 and as described above, a delivery catheter 40 is delivered to the venous system proximate the brain via the femoral or jugular vein. Catheter 40 is inserted into sigmoid sinus lumen 12 at a proximal location 13 toward the neck and inserted toward a distal end 15, which is toward the brain.

Delivery catheter 40 includes a second lumen 44 and a shunt delivery port 42. Lumen 44 directs the entire catheter to the correct location with for example, a guide wire, to allow injection of intravenous contrast to visualize the venous lumen. Lumen 44 also supports balloons 46 that can be deployed to temporarily occlude venous flow during stunt implantation. Shunt 20 is positioned at an end of an internal catheter 48 that is manipulated through catheter 40 and port 42. To prevent thrombosis within the sigmoid sinus and around the endovascular shunt, shunt 20 can be provided with an anti-thrombic coating.

As shown in FIG. 5, internal catheter 48 facilitates twisting of shunt 20 so that it penetrates through sigmoid sinus wall 12. Catheter 48 includes a hollow lumen to allow CSF withdrawal after shunt penetration of the sigmoid sinus wall to confirm that CSF is flowing through the shunt. However, catheter 48 must be rigid enough to allow twisting of the shunt such that it penetrates the sigmoid sinus wall. Upon insertion, helical tip 30 extends into cistern 18 and CSF located therein. A projection 28 located on shunt 20 between the ends abuts the wall and prevents the shunt from passing therethrough. Upon placement, internal catheter 48 is detached. The CSF can also be aspirated back prior to detachment of catheter 48.

Thereafter, delivery catheter 40 can be removed and shunt 20 is implanted as shown in FIG. 6. CSF 50 draining from outlet 36 from CSF space 18 is delivered to the venous blood flow 17 where it mixes with the blood and passes through the blood stream It also should be appreciated that shunt 20 can incorporate different tips at its end and different mechanisms for penetrating the dura.

Thus, the endovascular CSF shunt devices described herein can be placed into a patient percutaneously via a catheter inserted into the venous system of the body through a needle hole, without the need for open surgery, creating a burr hole in the skull, or passing a catheter through cerebellum to access a CSF-filled ventricle. In some patients, the device can be inserted without general anesthesia, which is not possible with current cerebrospinal fluid shunts. The device also will allow for more physiologic drainage of cerebrospinal fluid since the device is shunting cerebrospinal fluid into the same cerebral venous system that occurs naturally in normal people.

2 Shunt Stabilization

Specialized stabilization devices and delivery guide catheters have also been developed to facilitate implantation and stabilization of endovascular cerebral spinal fluid shunt (eCSFS) devices within the sigmoid sinus, transverse sinus, straight sinus, or sagittal sinus of a patient.

2.1 eCSFS Device Stabilization Devices

In certain situations, an eCSFS device which is implanted in a wall of the sigmoid sinus of a patient or other sinus described herein can migrate (e.g., dislodge) from the wall, degrading the ability of the eCSFS device to drain cerebral spinal fluid from the patient's subarachnoid space. In some examples, to address this problem, a stent-like device is used to anchor the eCSFS device into the wall of the aforementioned sinus and to provide a platform to prevent migration of the eCSFS device after deployment.

2.1.1 Self-Expanding Coil Type Stents

Figure 7:
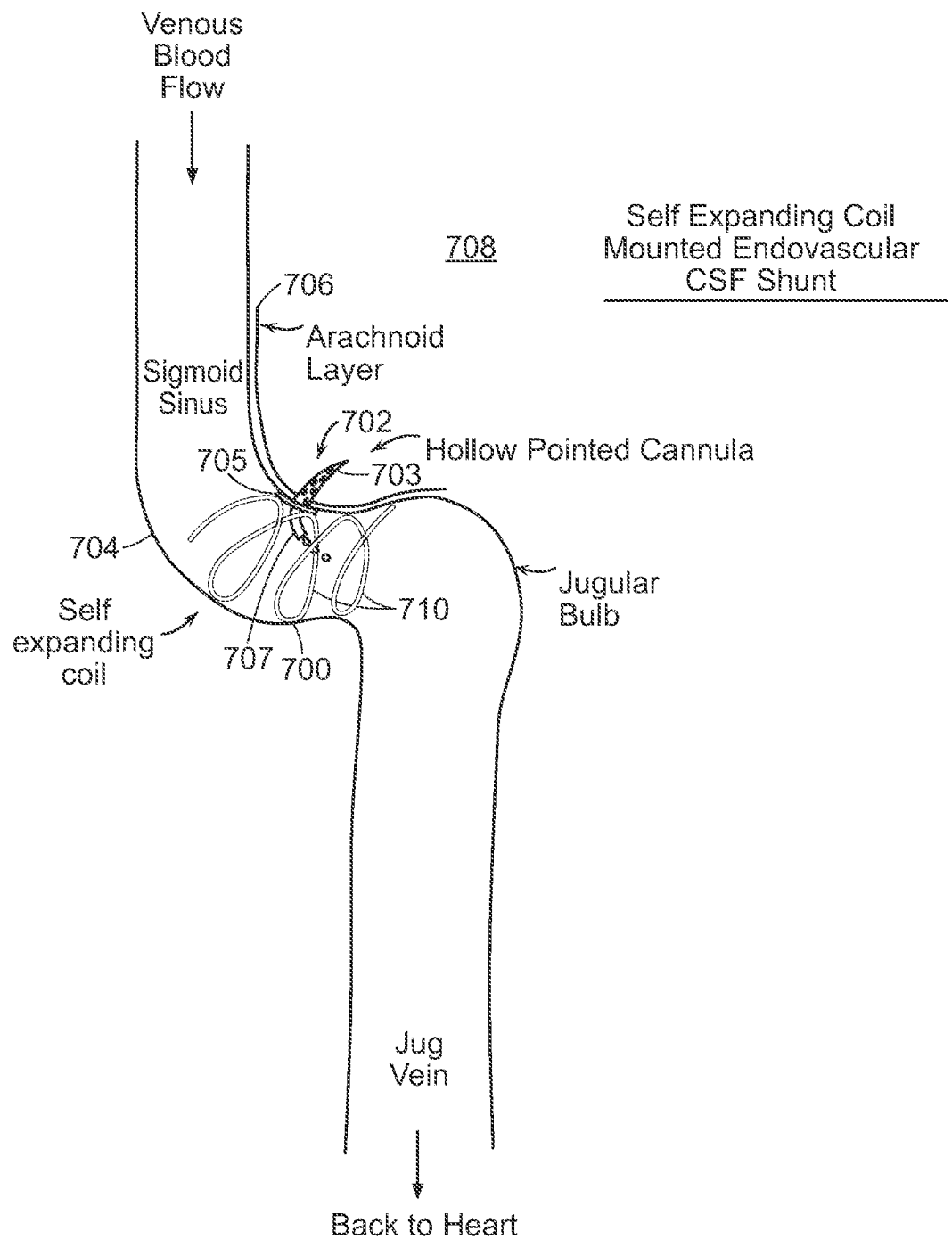
FIG. 7 shows a self-expanding coil type stent disposed within a sigmoid sinus.

Referring to FIG. 7, one example of a stent 700 is implemented as a self-expanding coil, which is coupled to an eCSFS device 702. In some examples, the eCSFS device 702 includes a hollow-pointed perforated cannula 703, a platform 705 including a flow control mechanism (e.g., a one-way valve), and a drainage tube 707. The stent 700 is deployed within the sigmoid sinus 704 of a patient with the hollow-pointed cannula 703 inserted through the wall of the sigmoid sinus 704, through the arachnoid layer 706, and into the patient's subarachnoid space 708. In the deployed state, CSF in the subarachnoid space 708 passes through the perforations in the hollow-pointed cannula 703, through the flow regulation mechanism in the platform 705, and out of the drainage tube 707 into the sigmoid sinus 704.

In general, the self-expanding coil type stent 700 is a coiled, spring-like member (e.g., a fine platinum or nitinol wire spring) which, when deployed, applies a constant outward radial force against the sigmoid sinus wall such that the stent 700 is anchored in place within the sigmoid sinus 704 by compressive force. Since the eCSFS device 702 is coupled to the stent 700, the stent 700 acts to anchor the eCSFS device 702 in place.

Furthermore, the outward radial force applied by the stent 700 presses the eCSFS device 702 against the sigmoid sinus wall, thereby further stabilizing the position of the eCSFS device 702 in the sigmoid sinus wall.

In some examples, to deploy the stent 700, the stent 700 is first compressed (e.g., by twisting the coiled, spring-like member to reduce its diameter) and then loaded into a delivery catheter. The delivery catheter is endovascularly guided to a desired location in the sigmoid sinus 704 or other sinus described herein. Once the delivery catheter, including the compressed stent 700 arrives at the desired location, the compressed stent is released into the sigmoid sinus 704, causing the stent to decompress. Upon decompression of the stent 700, the diameter of the stent increases until the stent 700 conforms to the inner surface of the sigmoid sinus 704.

In some examples, the decompression of the stent 700 is not sufficiently forceful to push the hollow-pointed cannula 703 through the wall of the sigmoid sinus 704 and through the arachnoid layer 706. In such examples, a force generating actuator (e.g., a balloon) is provided by the delivery catheter and inserted into the coils 710 of the stent 700, such that when expanded, the hollow-pointed cannula 703 is forced through the wall of the sigmoid sinus 704, through the arachnoid layer 706, and into the subarachnoid space 708.

2.1.2 Self-Expanding Circular Basket Type Stent

Figure 8:
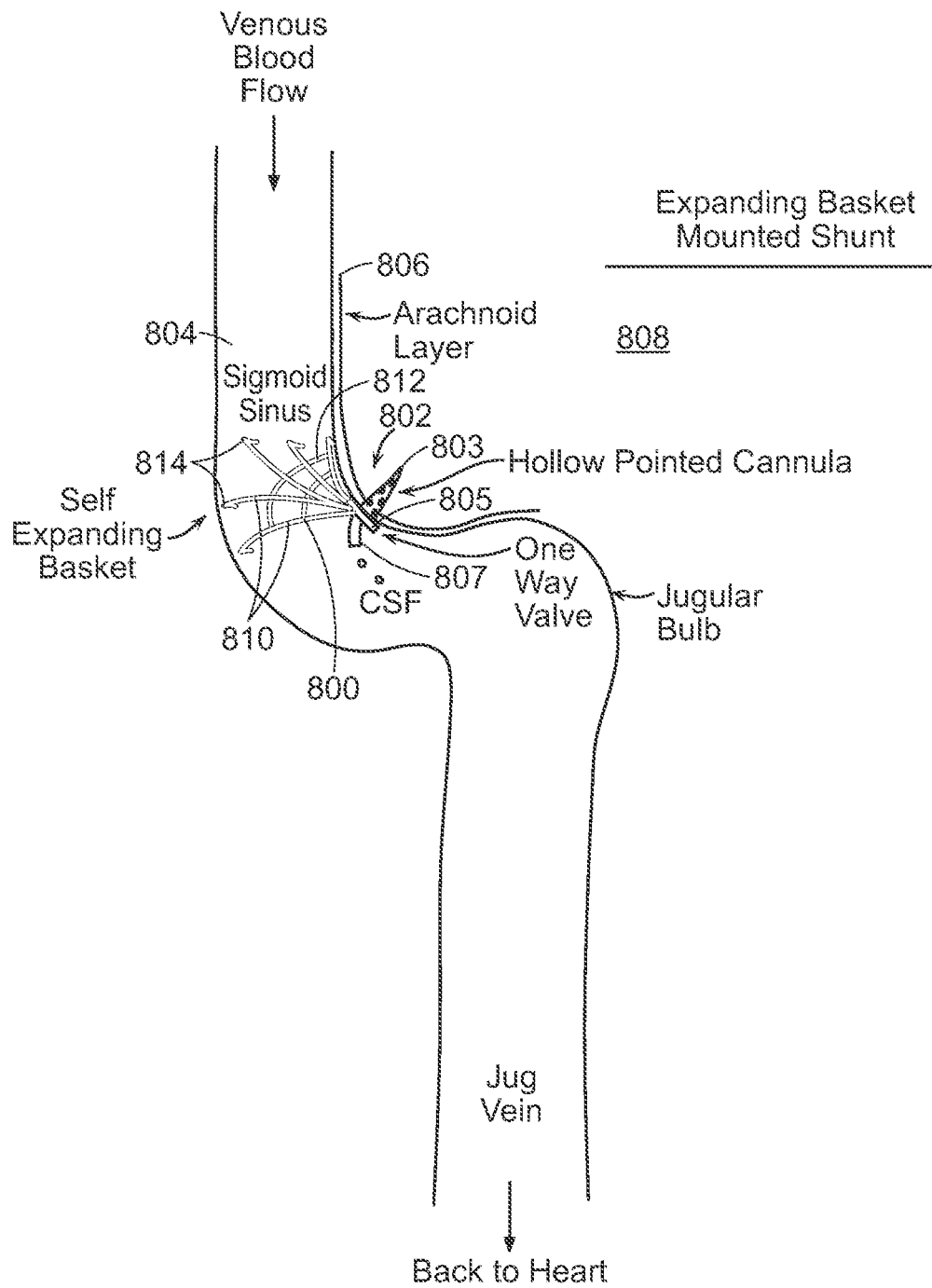
FIG. 8 shows an alternative embodiment of a self-expanding stent disposed within a sigmoid sinus.

Referring to FIG. 8, another example of a stent 800 is implemented as a self-expanding circular basket, which is coupled to an eCSFS device 802. In some examples, the eCSFS device 802 includes a hollow-pointed perforated cannula 803, a platform 805 including a flow control mechanism (e.g., a one-way valve), and a drainage tube 807. The stent 800 is deployed within the sigmoid sinus 804 of a patient with the hollow-pointed cannula 803 inserted through the wall of the sigmoid sinus 804, through the arachnoid layer 806, and into the patient's subarachnoid space 808. In the deployed state, cerebrospinal fluid in the subarachnoid space 808 passes through the perforations in the hollow-pointed cannula 803, through the flow regulation mechanism in the platform 805, and out of the drainage tube 807 into the sigmoid sinus 804.

In general, the stent 800 includes multiple collapsible tines 810 (e.g., thin platinum or nitinol wires) interconnected by webs 812 in a configuration similar to the support ribs of an umbrella. In some examples, the end of each tine 810 includes a barbed tip 814. When expanded, the tines 810 of the stent 810 make contact with the inner surface of the sigmoid sinus wall and the barbs 814 collectively anchor the stent 800 to the sigmoid sinus wall, thereby preventing the stent 800 and the eCSFS device 802 from becoming dislodged.

In some examples, to deploy the stent 800, the tines 810 of the stent 800 are first collapsed in a manner similar to closing an umbrella and the collapsed stent 800 is loaded into a delivery catheter. The delivery catheter is endovascularly guided to a desired location in the sigmoid sinus 804 or other sinus described herein. Once the delivery catheter, including the collapsed stent 800, arrives at the desired location, the collapsed stent 800 is released into the sigmoid sinus 804, wherein the tines 810 of the stent 800 open in a manner similar to an umbrella opening. Upon the opening of the tines 810, the barbed tips 814 of the tines 810 make contact with and latch into the inner surface of the sigmoid sinus 804, anchoring the stent 800 in place.

In some examples, the opening of the tines 810 of the stent 800 does not push the hollow-pointed cannula 803 through the wall of the sigmoid sinus 804 and through the arachnoid layer 806. In such examples, a force generating actuator (e.g., a balloon) is provided by the delivery catheter and positioned adjacent to the hollow pointed cannula 803, such that when expanded, the hollow-pointed cannula 803 is forced through the wall of the sigmoid sinus 804, through the arachnoid layer 806, and into the subarachnoid space 808.

2.1.3 Self-Expanding Circumferential Type Stent

Figure 9:
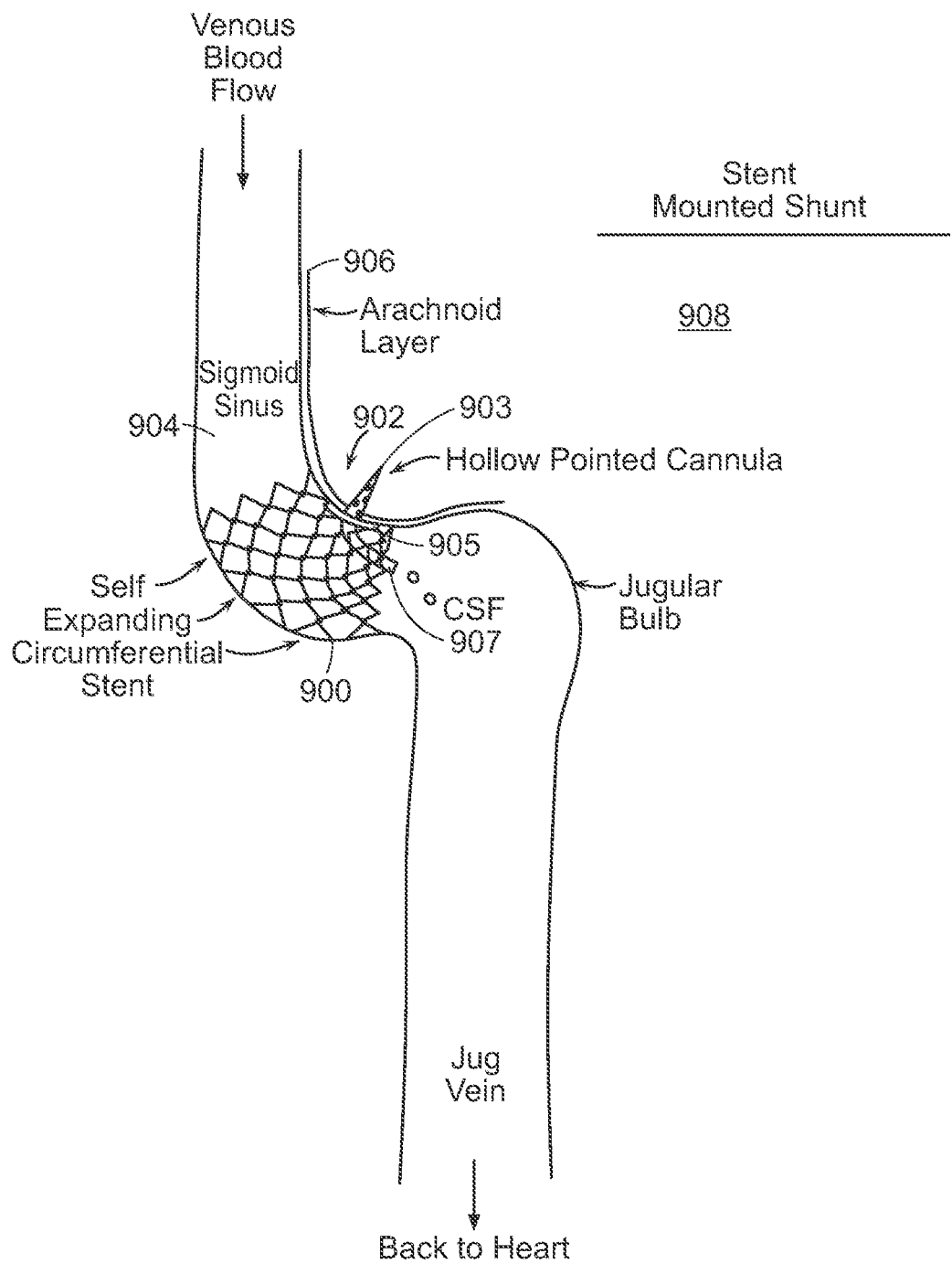
FIG. 9 shows yet another alternative embodiment of a self-expanding stent disposed within a sigmoid sinus.

Referring to FIG. 9, another example of a stent 900 is implemented as a self-expanding circumferential type stent, which is coupled to an eCSFS device 902. In some examples, the eCSFS device 902 includes a hollow-pointed perforated cannula 903, a platform 905 including a flow control mechanism (e.g., a one-way valve), and a drainage tube 907. The stent 900 is deployed within the sigmoid sinus 904 of a patient with the hollow-pointed cannula 903 inserted through the wall of the sigmoid sinus 904, through the arachnoid layer 906, and into the patient's subarachnoid space 908. In the deployed state, cerebrospinal fluid in the subarachnoid space 908 passes through the perforations in the hollow-pointed cannula 903, through the flow regulation mechanism in the platform 905, and out of the drainage tube 907 into the sigmoid sinus 904.

In general, the stent 900 has the form of a mesh tube (e.g., a tubular mesh of fine platinum or nitinol wire) which, when expanded, conforms to an inner surface of the sigmoid sinus 904. The expanded stent 900 applies a constant outward radial force against the sigmoid sinus wall such that the stent 900 is anchored in place within the sigmoid sinus 904 by compressive force. Since the eCSFS device 902 is coupled to the stent 900, the stent 900 also acts to anchor the eCSFS device 902 in place.

Furthermore, the outward radial force applied by the stent 900 presses the eCSFS device 902 against the sigmoid sinus wall, thereby further stabilizing the position of the eCSFS device 902 in the sigmoid sinus wall.

In some examples, to deploy the stent 900, the stent 900 is first compressed to reduce its diameter and fitted onto a force generating actuator (e.g., a balloon) provided by the delivery catheter. The delivery catheter is endovascularly guided to a desired location in the sigmoid sinus 904 or other sinus described herein. Once the delivery catheter with the compressed stent 900 fitted thereon reaches the desired location, the balloon of the delivery catheter is caused to expand, thereby expanding the stent 900 such that it conforms to the inner surface of the sigmoid sinus 904. The expansion of the balloon also forces the hollow-pointed cannula 903 through the wall of the sigmoid sinus 904, through the arachnoid layer 906, and into the subarachnoid space 908.

2.1.4 Self-Expanding Coil Type Stent

Figure 10:
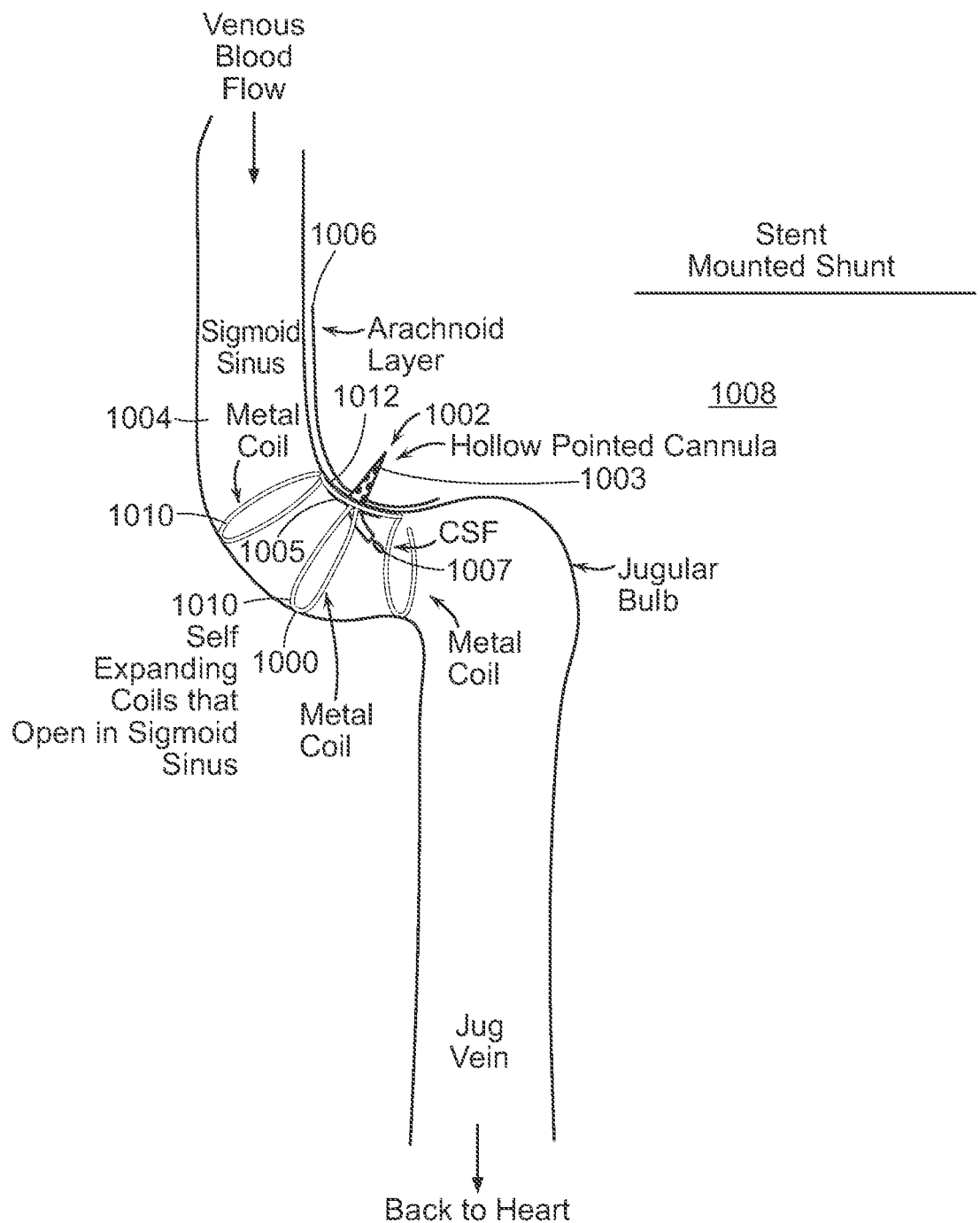
FIG. 10 shows a self-expanding coil type stent disposed within a sigmoid sinus.

Referring to FIG. 10, another example of a stent 1000 is implemented as a self-expanding coil type stent which includes a number of individual coils 1010 interconnected by one or more connecting members 1012 and coupled to an eCSFS device 1002. In some examples, the eCSFS device 1002 includes a hollow-pointed perforated cannula 1003, a platform 1005 including a flow control mechanism (e.g., a one-way valve), and a drainage tube 1007. The stent 1000 is deployed within the sigmoid sinus 1004 of a patient with the hollow-pointed cannula 1003 inserted through the wall of the sigmoid sinus 1004, through the arachnoid layer 1006, and into the patient's subarachnoid space 1008. In the deployed state, cerebrospinal fluid in the subarachnoid space 1008 passes through the perforations in the hollow-pointed cannula 1003, through the flow regulation mechanism in the platform 1005, and out of the drainage tube 1007 into the sigmoid sinus 1004.

In some examples, the individual coils 1010 of the stent 1000 are fine platinum or nitinol wire coils, which can expand to conform to an inner surface of the sigmoid sinus 1004. When deployed, the coils 1010 of the stent 1000 apply a constant outward radial force against the sigmoid sinus wall such that the stent 1000 is anchored in place within the sigmoid sinus 1004 by compressive force. Since the eCSFS device 1002 is coupled to the stent 1000, the stent 1000 also acts to anchor the eCSFS device 1002 in place.

Furthermore, the outward radial force applied by the stent 1000 presses the eCSFS device 1002 against the sigmoid sinus wall, thereby further stabilizing the position of the eCSFS device 1002 in the sigmoid sinus wall.

In some examples, to deploy the stent 1000, the stent 1000 is first compressed, including compressing each of the coils 1010 of the stent 1000 to reduce its diameter. The compressed stent 1000 is then loaded into a delivery catheter. The delivery catheter is endovascularly guided to a desired location in the sigmoid sinus 1004 or other sinus described herein. Once the delivery catheter, including the compressed stent 1000 arrives at the desired location, the compressed stent 1000 is released into the sigmoid sinus 1004, allowing the stent 1000, including the coils 1010 to decompress. Upon decompression of the stent 1000, the diameter of the coils 1010 increases until the coils 1010 conform to the inner surface of the sigmoid sinus 1004 at the delivery location.

In some examples, the decompression of the stent 1000 is not sufficiently forceful to push the hollow-pointed cannula 1003 through the wall of the sigmoid sinus 1004 and through the arachnoid layer 1006. In such examples, a force generating actuator (e.g., a balloon) is provided by the delivery catheter and inserted into the coils 1010 of the stent 1000 such that when expanded, the hollow-pointed cannula 1003 is forced through the wall of the sigmoid sinus 1004, through the arachnoid layer 1006, and into the subarachnoid space 1008.

2.1.5 Stent-Mounted Port

In some examples, one or more of the stents described above include a port structure attached to the stent. The port enables subsequent repositioning or revision of the cannula and/or flow control mechanism of the eCSFS device. That is, a stent guided stable port is first established between the sigmoid sinus (or other sinus described herein) and the intradural subarachnoid space. The port incorporates a self-sealing port to enable replacement of any cannula and/or flow control mechanisms without leaving an open puncture site between the sigmoid sinus and the subarachnoid space. In some examples, the port system obviates the need for multiple repeated punctures, especially when a cannula and/or flow control mechanism requires replacement.

Figure 11:
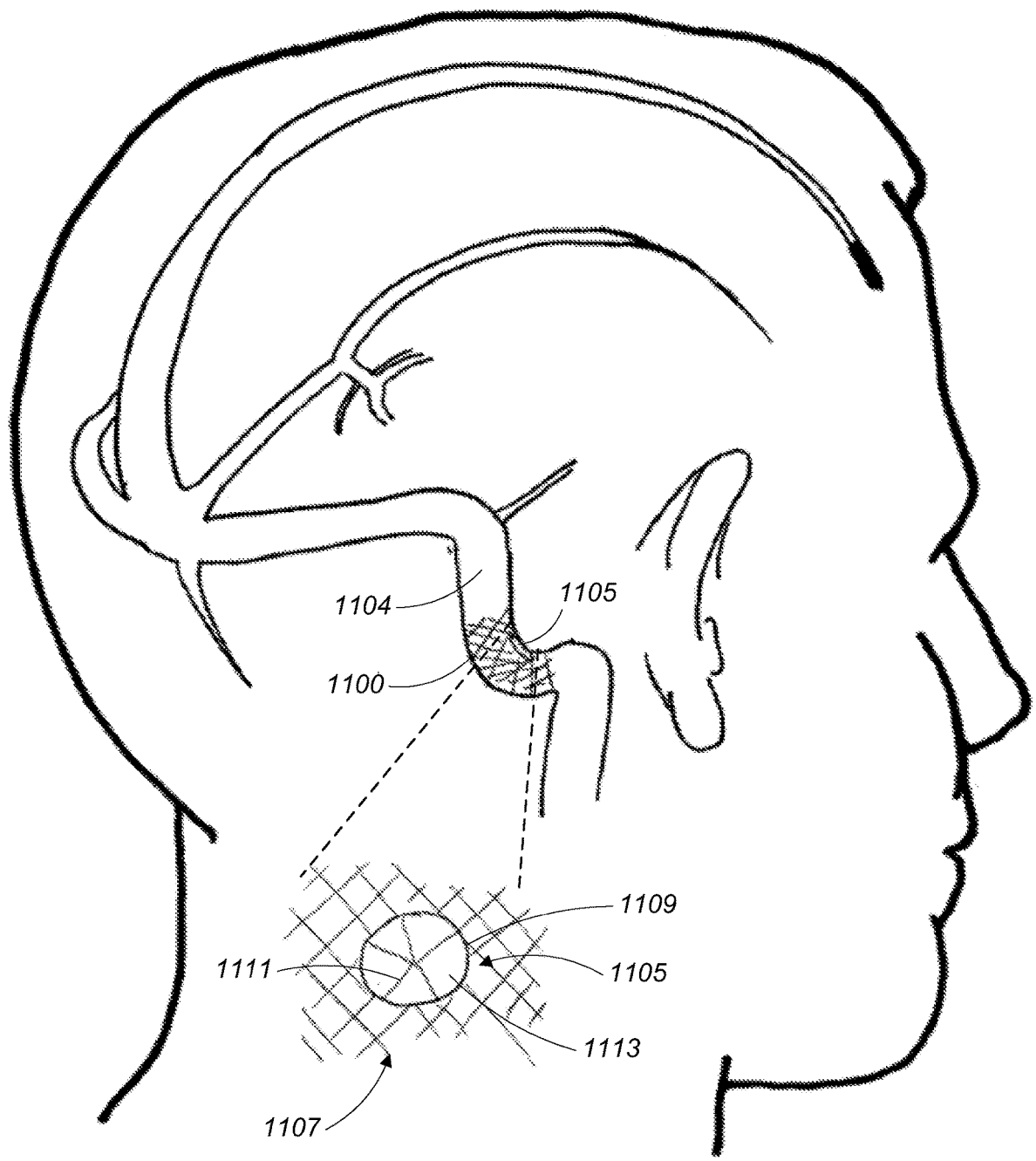
FIG. 11 shows a stent-mounted port disposed within a sigmoid sinus.

Referring to FIG. 11, a self-expanding circumferential type stent 1100 is deployed within the sigmoid sinus 1104 of a patient. A self-sealing port 1105 is mounted on the stent 1100 in such a way that the port 1105 is held against an inner surface of the patient's sigmoid sinus 1104. An expanded view 1107 of the port 1105 shows that, in some examples, the port 1105 includes a self-sealing, penetrable, antithrombotic membrane 1113 surrounded by a ring 1109.

In some examples, the membrane 1113 is penetrable due to a number of slits 1111 which are cut through the membrane 1113. The slits 1111 are cut in such a way (e.g., a spiral cut resembling that of a camera leaf shutter) that they sealingly close around any object inserted into the port 1105 and are sealingly closed when no object is inserted in the port 1105. In other examples, the membrane 1113 is a solid elastic membrane (e.g., silastic or a silicone based alternative) which, upon penetration by an object (e.g., an eCSFS device), forms a seal around the object and, upon removal of the object, reseals itself. In some examples, the membrane 1113 is fabricated using a material with inherent antithrombotic properties. In other examples, the membrane 1113 includes an antithrombotic coating.

In some examples, the ring 1109 is fabricated from material such as nitinol or platinum, possibly decorated with radiopaque material markers made of gold or tantalum or another suitably radiopaque material. In some examples, the ring 1109 includes, on its outer side, facing the inner surface of the patient's sigmoid sinus 1104, a groove with a hydrogel gasket (not shown) disposed therein. The outer side of the ring 1109 including the hydrogel gasket makes contact with the inner surface of the patient's sigmoid sinus 1104. Upon contact with sigmoid sinus blood, the hydrogel gasket swells, providing a hermetic seal that prevents sigmoid sinus blood from flowing around the port 1105 into the intracranial space.

Figure 12:
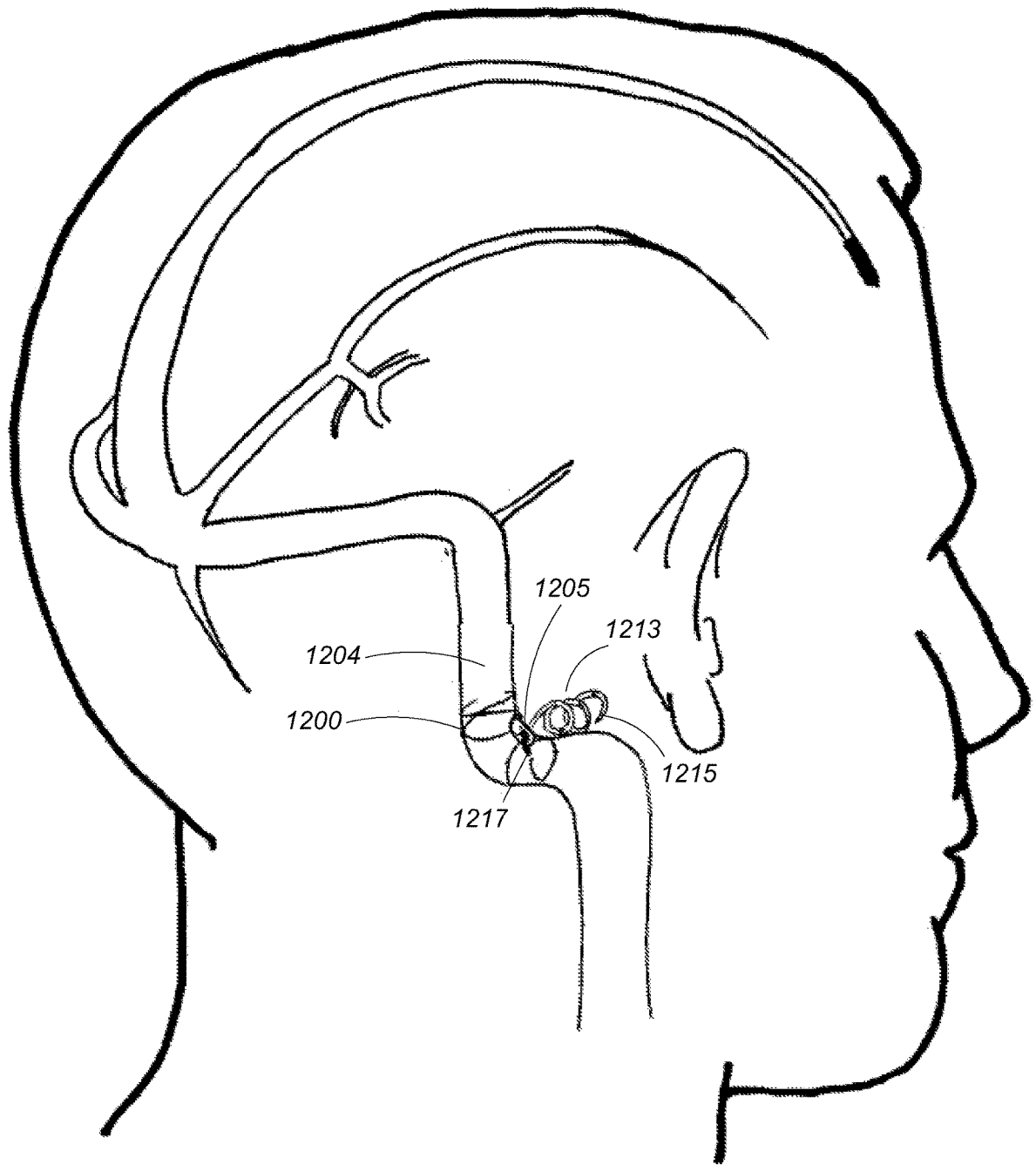
FIG. 12 shows a stent-mounted port disposed within a sigmoid sinus and having an endovascular cerebrospinal fluid shunt device inserted therein.

Referring to FIG. 12, a self-expanding coil type stent 1200 including a self-sealing port 1205 is deployed within the sigmoid sinus 1204 of a patient. An eCSFS device 1213 (e.g., a corkscrew type eCSFS device) is inserted through the port 1205 with its tip 1215 in the patient's subarachnoid space and its drainage tube 1217 located in the patient's sigmoid sinus 1204. Due to the above-described configuration of the port 1205, the eCSFS device 1213 can be removed and replaced without having to create another puncture site at a different location in the patient's sigmoid sinus wall. Furthermore, the port 1205 ensures that fluid passes only through the eCSFS device 1213 and does not leak into or out of the subarachnoid space through the puncture site.

In some examples, the port is deployed in a patient's sigmoid sinus with an eCSFS device already installed within the port apparatus. In other examples, the port is deployed in the patient's sigmoid sinus without an eCSFS device installed through the port and the eCSFS device is installed through the port in a later step.

2.1.6 Alternative Stent Configurations

In some examples, the stent devices described above may include slots or multiple miniature barbs which act to prevent migration of the stent within the smooth sinus endothelial layer of the sigmoid, transverse, straight, or sagittal sinus during and/or after deployment. In some examples, the surface of the stent may be treated such that its outer wall is abrasive and prevents slippage within the smooth endothelial layer during and/or after deployment.

In some examples, the stent devices described above are retrievable or repositionable after deployment. In some examples, the stent devices are constructed with an umbrella like mesh, providing the benefit of catching any foreign material that may be liberated or released by deployment of the eCSFS device. In some examples, the umbrella like mesh is retrievable through a specialized guide catheter.

In some examples, one or more of the stents described above includes a deployment mechanism including a controllable central sharp spicule that is hollow such that it allows passage of cerebrospinal fluid. This mechanism will enable the perforation of the sigmoid, transverse, straight, or sagittal sinus wall and while also allowing for the spicule to be retracted into the device and removed if necessary. For example, the spicule, included in an eCSFS device is inserted through a stent mounted, self-sealing port structure (as described above) and is held in place by friction in the self-sealing port structure. To remove the spicule, the eCSFS device including the spicule could be grabbed with an endovascular snare and pulled out of the self-sealing port structure and into the venous system.

3 Alternative eCSFS Device Configurations

In the above description the eCSFS device is described as having a corkscrew type intracranial aspect. However, other examples of eCSFS devices have been developed which allow safe placement of the device, stability of the device, penetration through the dura and arachnoid, apposition of the arachnoid to the dura after device deployment, and slight displacement of the brain parenchyma (e.g., the cerebellar cortex) so that it does not clog the device.

3.1.1 Corkscrew Type Self-Anchoring eCSFS Device

Figure 13:
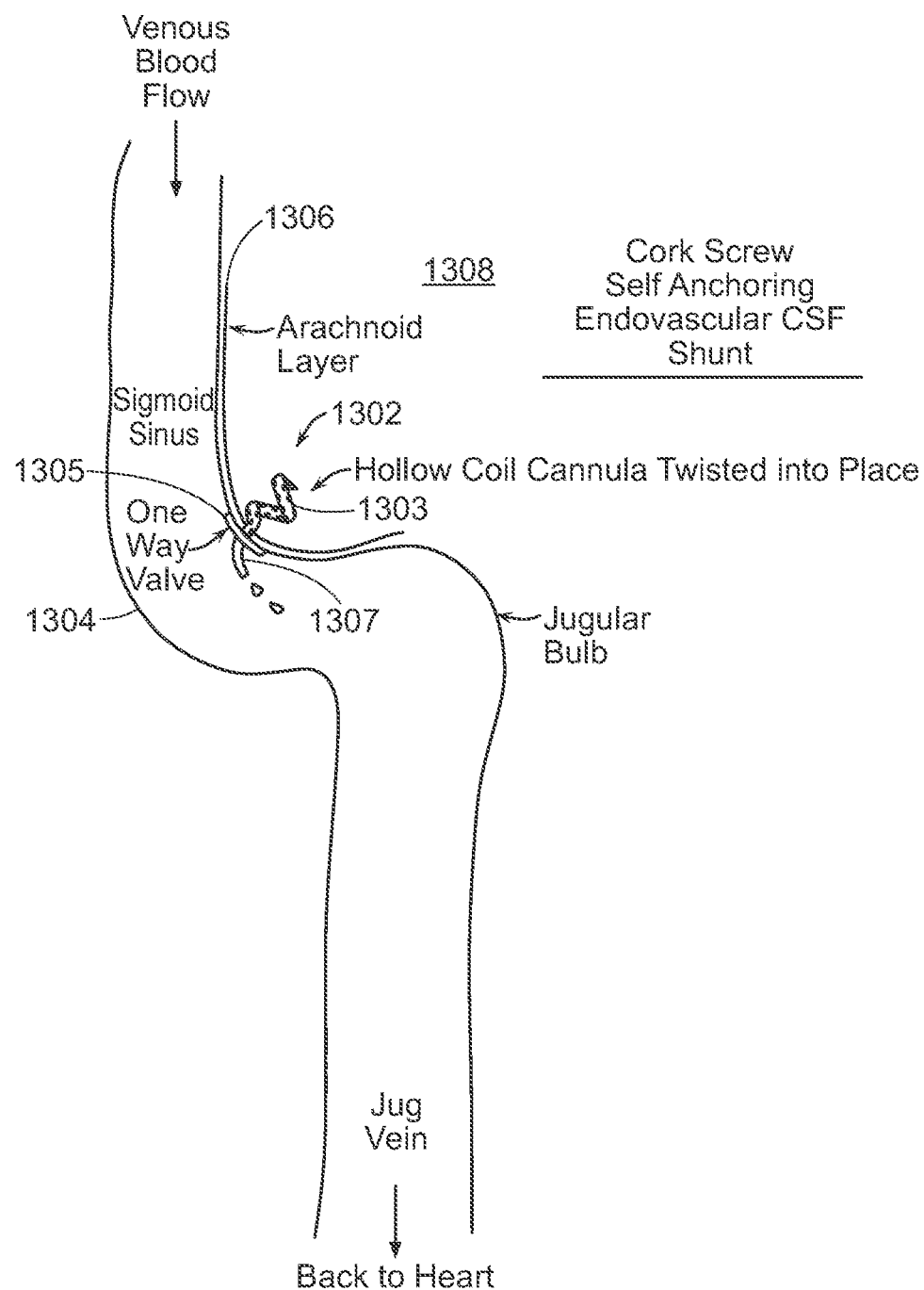
FIG. 13 shows a corkscrew type self-anchoring endovascular cerebrospinal fluid shunt device.

Referring to FIG. 13, a corkscrew type self-anchoring eCSFS device 1302 (similar to the corkscrew shaped shunt described above) includes a corkscrew shaped perforated cannula 1303, a platform 1305 including a flow regulation mechanism (not shown), and a drainage tube 1307. In its deployed state, the corkscrew-shaped cannula 1303 is inserted through a sigmoid sinus wall, through the arachnoid layer 1306, and into the subarachnoid space 1308 of a patient. Cerebrospinal fluid flows through the perforations of the corkscrew shaped cannula 1303, through the flow control mechanism in the platform 1305, and out of the drainage tube 1307 with the flow control mechanism controlling the flow of cerebrospinal fluid.

To deploy the corkscrew type self-anchoring eCSFS device 1302, the eCSFS device 1302 is first loaded into a delivery catheter. The delivery catheter endovascularly guides the eCSFS device 1302 to a desired deployment location in the sigmoid sinus 1304. Once at the desired location, the tip of the corkscrew type self-anchoring eCSFS device 1302 is pressed into a wall of the sigmoid sinus 1304 and the eCSFS device 1302 is rotated such that the corkscrew shaped cannula 1303 passes through with wall of the sigmoid sinus 1304 with a screw-like motion until the platform 1305 rests against the wall of the sigmoid sinus 1304 (or other sinus described herein). Once the eCSFS device 1302 is fully deployed, the delivery catheter is withdrawn from the patient.

In addition to the features described in earlier sections, in some examples, once deployed, the eCSFS device 1302 resists withdrawal from sigmoid sinus wall due to the corkscrew shape of its cannula 1303.

3.1.2 Three-Dimensional Coil Type Self-Anchoring eCSFS Device

Figure 14:
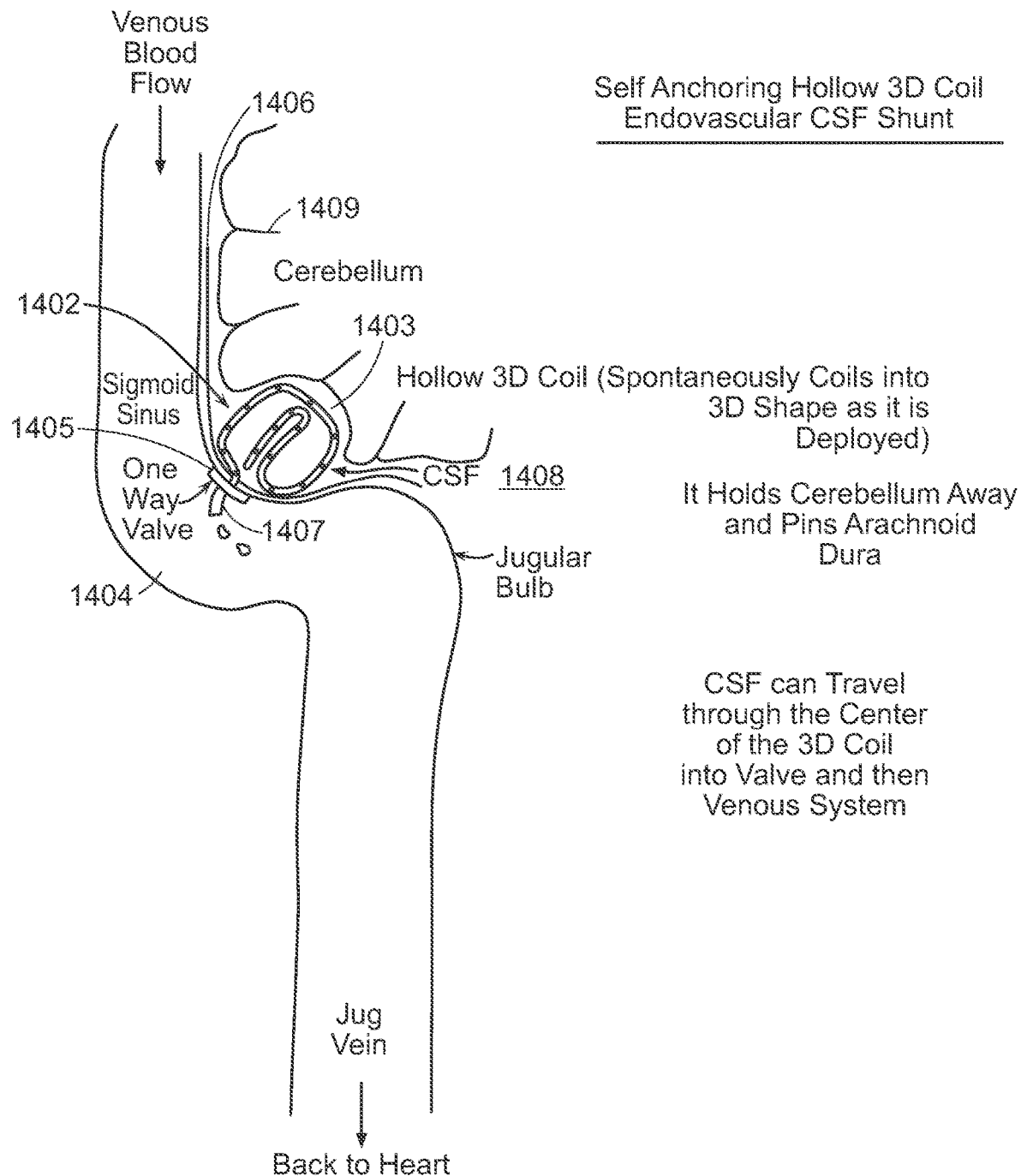
FIG. 14 shows three-dimensional coil type self-anchoring endovascular cerebrospinal fluid shunt device.

Referring to FIG. 14, a three-dimensional coil type self-anchoring eCSFS device 1402 includes a section of coiled three-dimensional-shaped perforated microcatheter tubing 1403 with a pre-defined three-dimensional coil shape, a platform 1405 including a flow regulation mechanism (e.g., a one-way valve), and a drainage tube 1407. In its deployed state, the perforated tubing 1403 is disposed through a sigmoid sinus wall and into the subarachnoid space 1408 of a patient, between the brain parenchyma 1409 and the arachnoid layer 1406. Cerebrospinal fluid flows through the perforations of the tubing 1403, through the flow control mechanism in the platform 1405, and out of the drainage tube 1407 with the flow regulation mechanism controlling the flow of cerebrospinal fluid.

In general, the three-dimensional shape of the tubing 1403 presses against the arachnoid layer 1406, causing the platform 1405 to be pulled tight against the wall of the sigmoid sinus 1404. This pulling of the platform 1405 by the tubing 1403 pinches the sigmoid sinus wall and the arachnoid layer 1406 between the platform 1405 and the tubing 1403, anchoring the eCSFS device 1402 in place.

In some examples, the three-dimensional shape of the tubing 1403 pushes against the brain parenchyma 1409 to create a space for cerebrospinal fluid to pool around the tubing 1403. In general, at least some portions of the tubing 1403, along with the perforations in the tubing, are not in contact with the brain parenchyma 1409. The portions of the tubing 1403 not in contact with the brain parenchyma 1409 are less likely to become occluded and provide a consistently open, low resistance passageway for cerebrospinal fluid to flow through the valve and out of the drainage tube 1407.

In some examples, to deploy the three dimensional coil type self-anchoring eCSFS device 1402, the tubing 1403 of the device 1402 is first straightened out and loaded into a delivery catheter. The delivery catheter is endovascularly guided to a desired location in the sigmoid sinus 1404 or other sinus described herein. Once the delivery catheter including the device 1402 reaches the desired location, the tubing 1403 is pressed through the wall of the sigmoid sinus 1404, through the arachnoid layer 1406, and into the subarachnoid space 1408. In some examples, the tubing 1403 is made from a material with shape memory properties such as nitinol (i.e., nickel titanium). In such examples, as the tubing is fed into the subarachnoid space 1408 (or shortly thereafter), the tubing reverts to its original, predefined three-dimensional coil shape, pushing against the brain parenchyma 1409 as is described above.

3.1.3 Umbrella Type Self-Anchoring eCSFS Device

Figure 15:
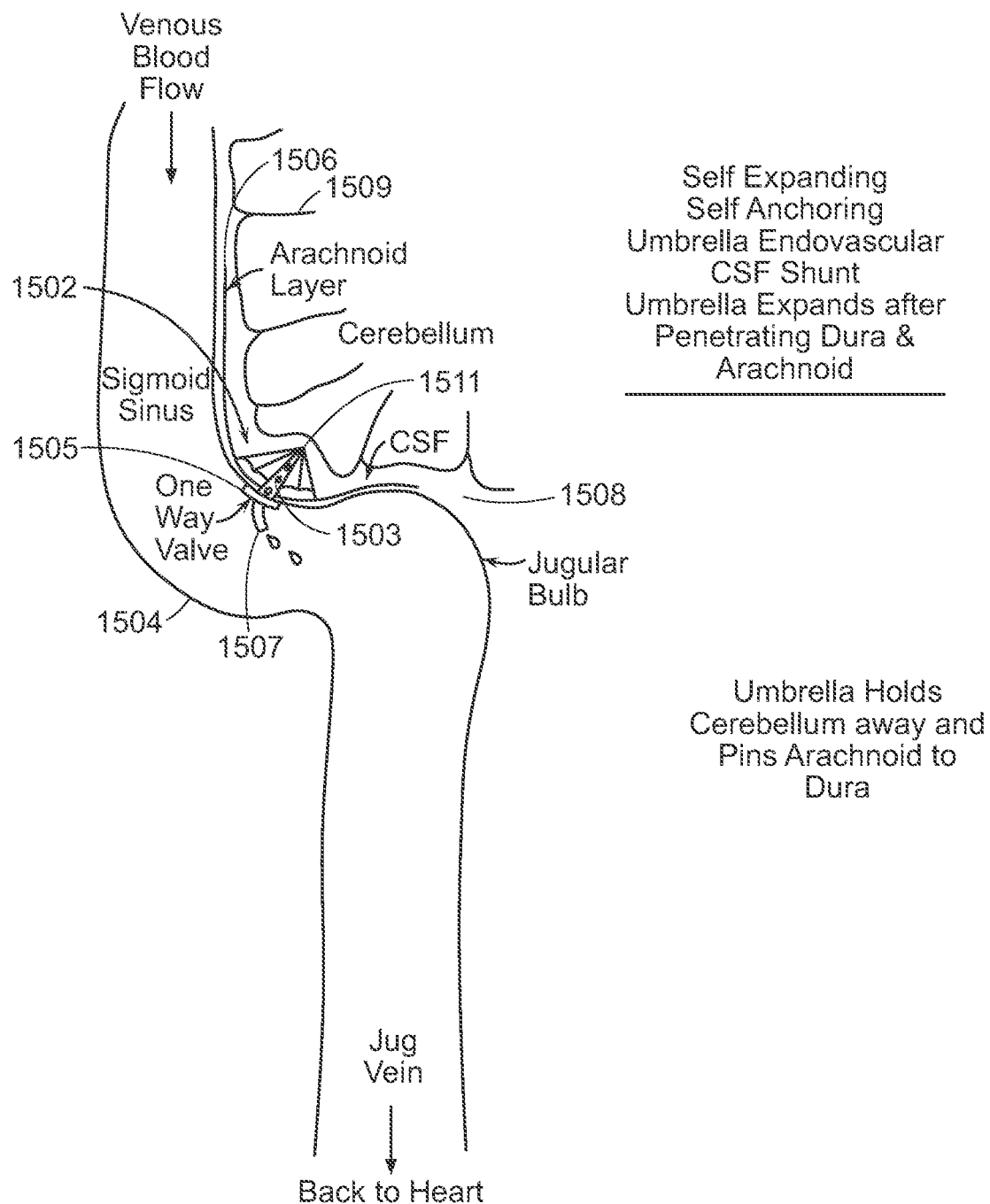
FIG. 15 shows an umbrella type self-anchoring endovascular cerebrospinal fluid shunt.

Referring to FIG. 15, an umbrella type self-anchoring eCSFS device 1502 includes an umbrella shaped screen 1511 covering a perforated hollow cannula 1503, a platform 1505 including a flow regulation mechanism (e.g., a one-way valve), and a drainage tube 1507. In its deployed state, the perforated hollow cannula 1503 and the umbrella shaped screen 1511 are disposed through a sigmoid sinus wall into the subarachnoid space 1408 of a patient, between the brain parenchyma 1509 and the arachnoid layer 1506. Cerebrospinal fluid flows through the perforations of the cannula 1503, through the flow regulation mechanism in the platform 1505, and out of the drainage tube 1507 into the sigmoid sinus 1504 with the flow regulation mechanism controlling the flow of cerebrospinal fluid.

In general, the umbrella shaped screen 1511 presses against the arachnoid layer 1506, causing the platform 1505 to be pulled tight against the wall of the sigmoid sinus 1504. This pulling of the platform 1505 by the umbrella shaped screen 1511 pinches the sigmoid sinus wall and the arachnoid layer 1506 between the platform 1505 and the umbrella shaped screen 1511, anchoring the eCSFS device 1502 in place.

In some examples, the umbrella shaped screen 1511 pushes against the brain parenchyma 1509 to create a space for cerebrospinal fluid to pool around the perforated hollow cannula 1503. In general, the umbrella shaped screen 1511 prevents the brain parenchyma 1509 from making contact with and occluding the perforations in the perforated hollow cannula 1503, thereby maintaining a consistently open, low resistance passageway for cerebrospinal fluid to flow through the valve and out of the drainage tube 1507.

In some examples, to deploy the umbrella type self-anchoring eCSFS device 1502, the umbrella shaped screen 1511 is collapsed in a manner similar to an umbrella being collapsed and the device 1502 is loaded into a delivery catheter. The delivery catheter is endovascularly guided to a desired location in the sigmoid sinus 1504 or other sinus described herein. Once the delivery catheter including the device 1502 reaches the desired location, the perforated hollow cannula 1503 and the collapsed umbrella shaped screen 1511 are pressed through the wall of the sigmoid sinus 1504, through the arachnoid layer 1506, and into the subarachnoid space 1508. In some examples, the umbrella shaped screen 1511 is made from a material with shape memory properties such as nitinol (i.e., nickel titanium). In such examples, once the umbrella shaped screen 1511 is fully fed into the subarachnoid space 1508 (or shortly thereafter), the umbrella shaped screen 1511 opens to its original, predefined umbrella shape, pushing against the brain parenchyma 1509 as described above. In other examples, once the umbrella shaped screen 1511 is fully fed into the subarachnoid space 1504, the umbrella shaped screen 1511 is mechanically opened by an endovascular surgeon operating the delivery catheter.

In some examples, the umbrella type self-anchoring eCSFS device 1502 can be included as part of one or more of the stents described above.

3.1.4 Globe Type Self-Anchoring eCSFS Device

Figure 16:
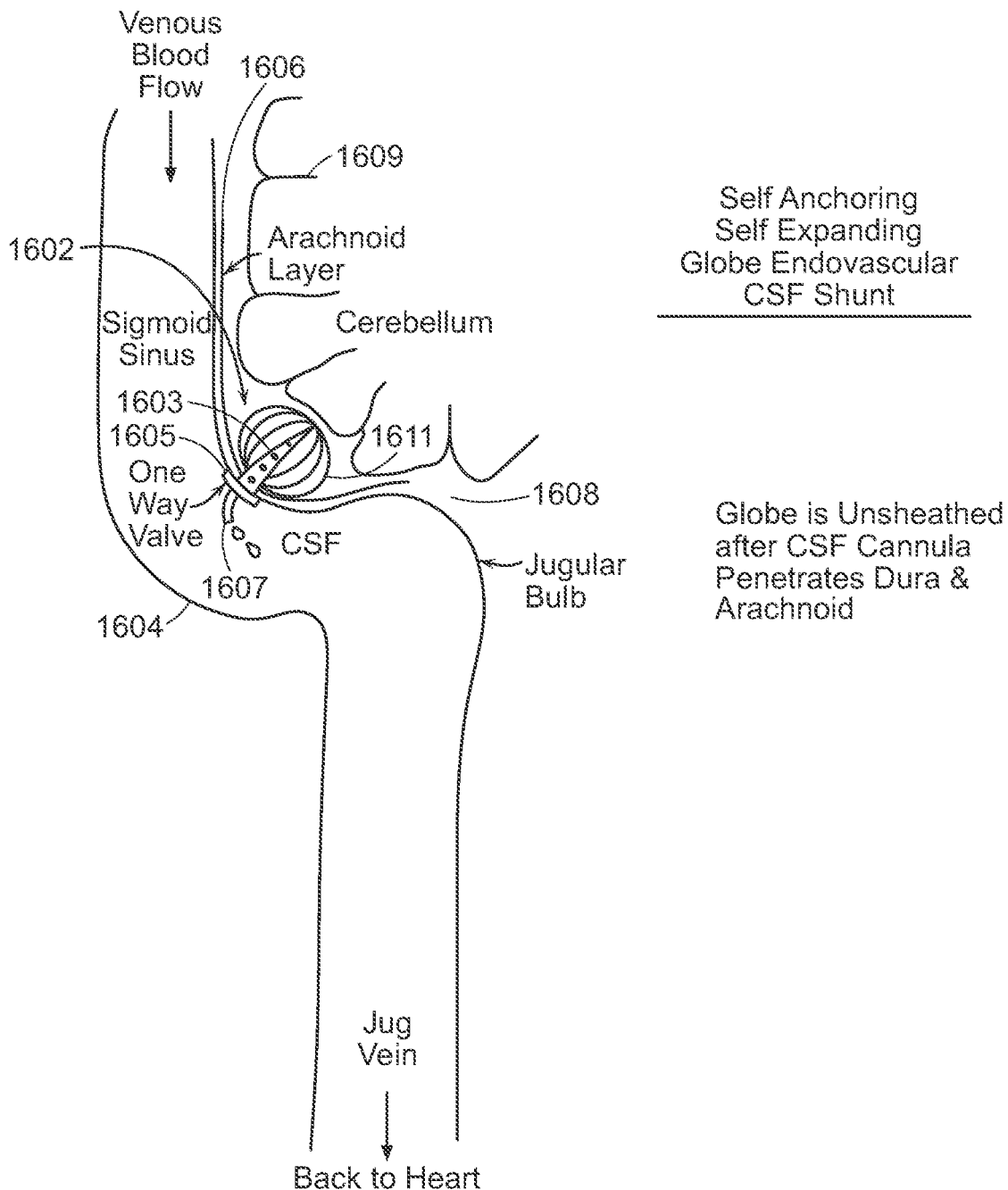
FIG. 16 shows a first globe type self-anchoring endovascular cerebrospinal fluid shunt device.

Referring to FIG. 16, a globe type self-anchoring eCSFS device 1602 includes a multi-filament globe-like assembly 1611 surrounding a perforated hollow cannula 1603, a platform 1605 including a flow regulation mechanism (e.g., a one-way valve), and a drainage tube 1607. In its deployed state, the perforated hollow cannula 1603 and the multi-filament globe-like assembly 1611 are disposed through a sigmoid sinus wall into the subarachnoid space 1608 of a patient, between the brain parenchyma 1609 and the arachnoid layer 1606. Cerebrospinal fluid flows through the perforations of the cannula 1603, through flow regulation mechanism in the platform 1605, and out of the drainage tube 1607 into the sigmoid sinus 1605 with the flow regulation mechanism controlling the flow of cerebrospinal fluid.

In general, the multi-filament globe-like assembly 1611 presses against the arachnoid layer 1606, causing the platform 1605 to be pulled tight against the wall of the sigmoid sinus 1605. This pulling of the platform 1605 by the multi-filament globe-like assembly 1611 pinches the sigmoid sinus wall and the arachnoid layer 1606 between the platform 1605 and the multi-filament globe-like assembly 1611, anchoring the eCSFS device 1602 in place.

In some examples, the multi-filament globe-like assembly 1611 pushes against the brain parenchyma 1609 to create a space for cerebrospinal fluid to pool around the perforated hollow cannula 1603. In general, the multi-filament globe-like assembly 1611 prevents the brain parenchyma 1609 from making contact with and occluding the perforations in the perforated hollow cannula 1603, thereby maintaining a consistently open, low resistance passageway for cerebrospinal fluid to flow through the valve and out of the drainage tube 1607.

In some examples, the multi-filament globe-like assembly 1611 can be made in different sizes and different shapes with different radial strengths.

To deploy the globe type self-anchoring eCSFS device 1602, the filaments of the globe-like assembly 1611 are first compressed and the device 1602 is loaded into a delivery catheter. The delivery catheter is endovascularly guided to a desired location in the sigmoid sinus or other sinus described herein. Once the delivery catheter including the device 1602 reaches the desired location, the compressed globe-like assembly 1611 and the perforated hollow cannula 1603 are pressed through the wall of the sigmoid sinus, through the arachnoid layer, and into the subarachnoid space. In some examples, the filaments of the globe-like assembly 1611 are made from a material with shape memory properties such as nitinol (i.e., nickel titanium). In such examples, once the globe-like assembly 1611 is fully fed into the subarachnoid space (or shortly thereafter), the globe-like assembly 1611 is gradually unsheathed, allowing the filaments of the globe-like assembly 1611 to return to their original, predefined globe-like shape, pushing against the brain parenchyma as described above.

Figure 17:
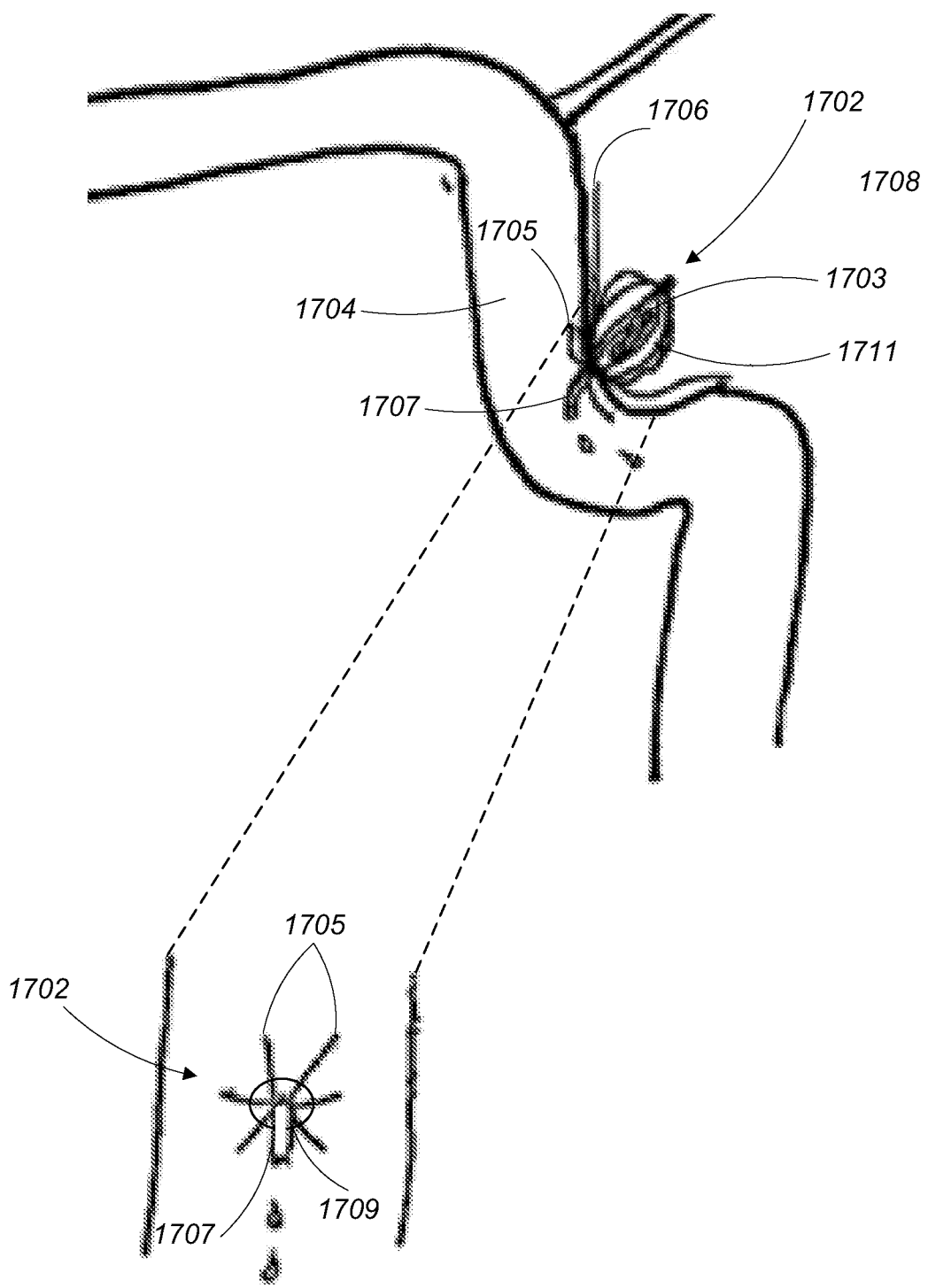
FIG. 17 shows a second globe type self-anchoring endovascular cerebrospinal fluid shunt device.

Referring to FIG. 17, another example of a globe type self-anchoring eCSFS device 1702 includes a multi-filament globe-like assembly 1711 surrounding a perforated hollow cannula 1703, a number of radial struts 1705, a platform 1709 including a flow regulation mechanism (e.g., a one-way valve), and a drainage tube 1707. In its deployed state, the perforated hollow cannula 1703 and the multi-filament globe-like assembly 1711 are disposed through a sigmoid sinus wall into the subarachnoid space 1708 of a patient, between the brain parenchyma (not shown) and the arachnoid layer 1706. Cerebrospinal fluid flows through the perforations of the cannula 1703, through the flow regulation portion in the platform 1709 and out of the drainage tube 1707 into the sigmoid sinus 1704 with the flow regulation mechanism controlling the flow of cerebrospinal fluid.

In general, the multi-filament globe-like assembly 1711 presses against the arachnoid layer 1706, causing the platform 1709 and the radial struts 1705 to be pulled tight against the wall of the sigmoid sinus 1705. This pulling of the platform 1709 and the radial struts 1705 by the multi-filament globe-like assembly 1711 pinches the sigmoid sinus wall and the arachnoid layer 1706 between the multi-filament globe-like assembly 1711 and the platform 1079 and radial struts 1705, anchoring the eCSFS device 1702 in place.

In some examples, to deploy the globe type self-anchoring eCSFS device 1702, the filaments, including the radial struts 1705 of the globe-like assembly 1711 are first compressed and the device 1702 is loaded into a delivery catheter. When compressed within the delivery catheter, the radial struts 1705 are in a straightened state where they extend along an axial direction of the eCSFS device 1702 rather than along a radial direction of the eCSFS device 1702. The delivery catheter is endovascularly guided to a desired location in the sigmoid sinus 1704 or other sinus described herein. Once the delivery catheter including the device 1702 reaches the desired location, the compressed globe-like assembly 1711 and the perforated hollow cannula 1703 are pressed through the wall of the sigmoid sinus, through the arachnoid layer, and into the subarachnoid space. In some examples, the filaments of the globe-like assembly 1711, including the radial struts 1705 are made from a material with shape memory properties such as nitinol (i.e., nickel titanium). In such examples, once the globe-like assembly is fully fed into the subarachnoid space (or shortly thereafter), the globe-like assembly 1711 is gradually unsheathed. When unsheathed, the filaments of the globe-like assembly 1711 are allowed to return to their original, predefined globe-like shape, pushing against the brain parenchyma as described above. Similarly, when unsheathed, the radial struts 1705 return to their original, predefined radially extending shape, pinching the sigmoid sinus wall between the radial struts 1705 and the globe-like assembly.

In some examples, rather than automatically returning to its original shape when unsheathed, the globe-like assembly 1711 is forced into its original, globe-like, shape by a surgeon (or another operator) pulling on a filament such as a wire which is attached to the top of the globe. In some examples, the eCSFS device 1702 includes a mesh or screen-like material which surrounds some or all of the globe-like assembly 1711, thereby preventing brain parenchyma from entering the globe-like assembly 1711 where it could potentially occlude the perforations of the cannula 1703.

3.1.5 Alternative eCSFS Device Configurations

In some examples, one or more of the eCSFS devices described above includes a self-sealing mechanism which prevents sinus blood (i.e., from the sigmoid, transverse, straight, or sagittal sinus) from flowing around the platform of the device into the intracranial space. For example, the platform of the device may include a groove formed in its surface facing the sigmoid sinus wall and a hydrogel gasket disposed within the groove. Upon contact with sigmoid sinus blood, the hydrogel gasket swells, providing a hermetic seal which prevents sigmoid sinus blood from flowing around the platform and into the intracranial space.

In some examples, the drainage tube of the eCSFS devices described above may extend along the internal jugular vein for a certain length, effectively mimicking a ventriculo-atrial shunt. In some examples, drainage tube of the eCSFS devices described above may be sufficiently distant from the venous sinus wall to prevent its incorporation and subsequent endothelialization in to the wall, which would result in occlusion of the eCSFS device.

In some examples the dimensions of the intracranial portions of the eCSFS devices described above are in the range of 3 mm to 1.5 cm. In some examples, the portions of the eCSFS devices described above which are located in the sigmoid sinus lumen have a dimension of approximately 2 mm to 4 mm. In some examples, the length of the drainage tubes of the eCSFS devices described above is configurable such that it reaches the superior vena cava and right atrial junction. In some examples, the eCSFS devices described herein have a length in the range of 4 to 5 centimeters.

In some examples, the eCSFS devices (and in particular, the drainage tube and the flow regulation mechanism) have a minimum diameter of 0.5 mm to minimize occlusion of the device by plaque, protein clots, and/or blood clots.

In some examples, the eCSFS devices are safe for use in a magnetic resonance imaging (MRI) machine.

In some examples, the eCSFS devices are removable and/or adjustable using a loop or snare device.

In some examples, multiple eCSFS devices can be placed adjacently (i.e., within 1 mm to 5 mm) in the sigmoid sinus.

In some examples, the platforms of the eCSFS devices described herein is made of a material with shape memory properties such as nitinol (i.e., nickel titanium).

In some examples, portions of the eCSFS device which are deployed in the lumen of the sigmoid sinus (e.g., the platform and the drainage tube) are coated in an anticoagulant material such as heparin to prevent clotting of blood in, on, and around the portions of the eCSFS device.

In some examples, the eCSFS device includes a mechanism for detecting whether cerebrospinal fluid is flowing through the device and wirelessly communicating that information to a technician. For example, the platform or the cannula of the device may include a flow sensor which senses whether cerebrospinal fluid is flowing through the device and, in some examples, the flow rate of cerebrospinal fluid. Data collected using the flow sensor can be provided to wireless communication circuitry in the device which, upon request, wirelessly communicates the flow sensor data out of the patient's body to a communication device operated by the technician. For example, the device may include RFID circuitry which is temporarily energized by radio frequency energy provided from outside of the patient's body. Once energized, the RFID circuitry uses the flow sensor to collect data related to the flow of cerebrospinal fluid through the device. The RFID circuitry then transmits the collected data out of the patient's body using radio frequency communications before it runs out of energy.

In some examples, the flow regulation valve in the platform of the device can be controlled (e.g., turned on, turned off, or adjusted) from outside of the patient's body (e.g., by using for example a magnet).

In some examples, the length of the drainage tube extending from the platform into the venous system can be controlled as can be the diameter of the perforations in the hollow cannula in order to affect the rate of flow of cerebrospinal fluid into the shunt. In some examples, a pressure gradient across the eCSFS device can be regulated by the use of valves with different pressure settings.

In some examples, the eCSFS devices described above are designed with an optimal flow rate of approximately 10 cubic centimeters (cc) of cerebrospinal fluid per hour (i.e., 200 cc-300 cc per 24 hour period).

In some examples, the eCSFS devices described above are designed to allow continuous flow of cerebrospinal fluid. In other examples, the eCSFS devices described above are designed for intermittent flow of cerebrospinal fluid.

In general, all of the eCSFS devices described above include flow regulation mechanism such as a one-way valve.

Although the present disclosure has been described in relation to particular embodiments thereof, many other variations and modifications and other uses will become apparent to those skilled in the art. It is preferred therefore, that the present disclosure be limited not by the specific embodiments and implementations described herein, but only by the appended claims.

4 Catheterization Apparatus

In some examples, delivery of an eCSFS device may require a catheterization apparatus that is specially designed for implantation of the eCSFS device in the sigmoid, transverse, straight, or sagittal sinus. For example, some patients such as those with a contralateral sinus stenosis or occlusion have a compromised alternative venous pathway. For these patients, full occlusion of the sigmoid sinus by, for example, a balloon guide of a guide catheter might severely reduce or completely inhibit venous drainage of the cerebral tissue. Such a reduction in venous drainage for an extended period of time such as the time required to implant an eCSFS device is potentially dangerous for the patient.

Figure 18:
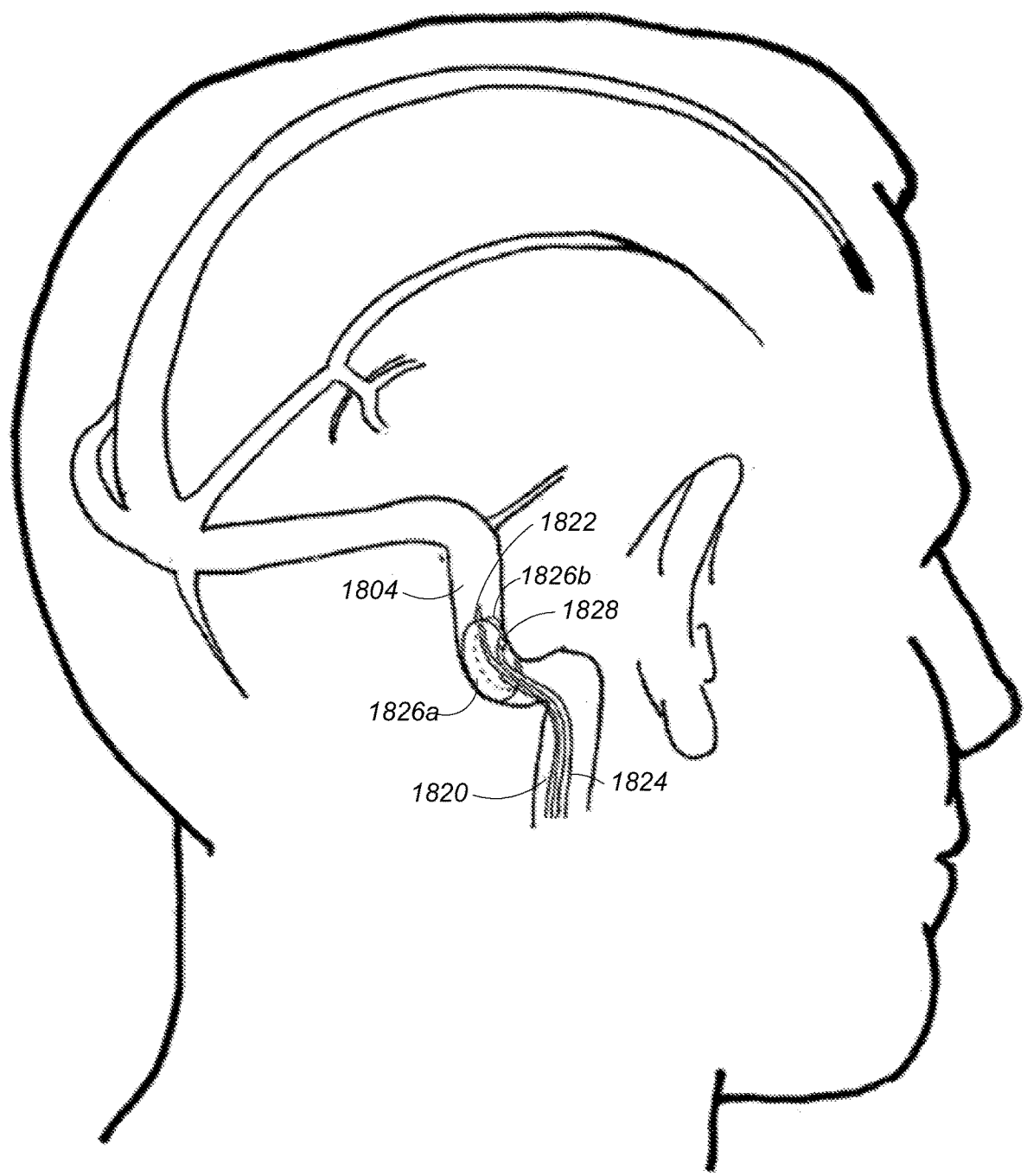
FIG. 18 shows a schematic of a catheterization apparatus inserted within a patient's sigmoid sinus with its stabilization balloons inflated.

Referring to FIG. 18 a catheterization apparatus 1820 includes a guide catheter 1822, a delivery catheter 1824, and two (or more) stabilization balloons 1826a, 1826b. Very generally, the guide catheter 1822 is used to endovascularly guide the catheterization apparatus 1820 to the sigmoid sinus 1804 (or other sinus described herein). While the catheterization apparatus 1820 is being guided to the delivery location, the stabilization balloons 1826a, 1826b are deflated. Once the catheterization apparatus 1820 arrives at the delivery location, the stabilization balloons 1826a, 1826b are inflated, stabilizing the catheterization apparatus 1820 at the delivery location and causing an opening 1828 of the delivery catheter 1824 to be positioned against an inner surface of a patient's sigmoid sinus 1804.

Figure 19:
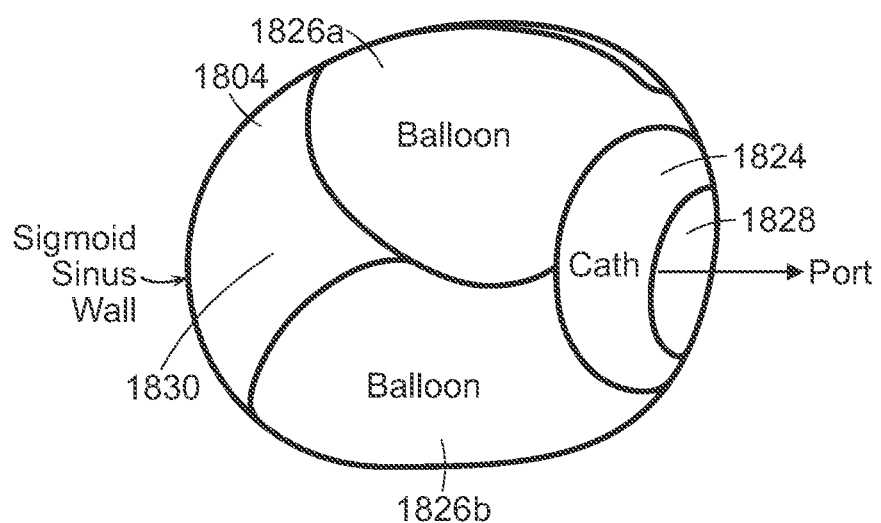
FIG. 19 shows a cross-sectional view of the catheterization apparatus of FIG. 18.

Referring to FIG. 19, a cross-sectional view of the end of the catheterization apparatus 1820 of FIG. 18 is shown. In the cross-sectional view, the catheterization apparatus 1820 is located within the sigmoid sinus 1804 with its stabilization balloons 1826a, 1826b inflated and the opening 1828 of the delivery catheter 1824 positioned against the inner surface of the patient's sigmoid sinus 1804. Due to the use of two (or more) stabilization balloons 1826a, 1826b, a significant portion 1830 of the lumen of the sigmoid sinus 1804 remains unoccluded, allowing for the passage of blood through the sigmoid sinus 1804 during the eCSFS device implantation procedure.

Figure 20:
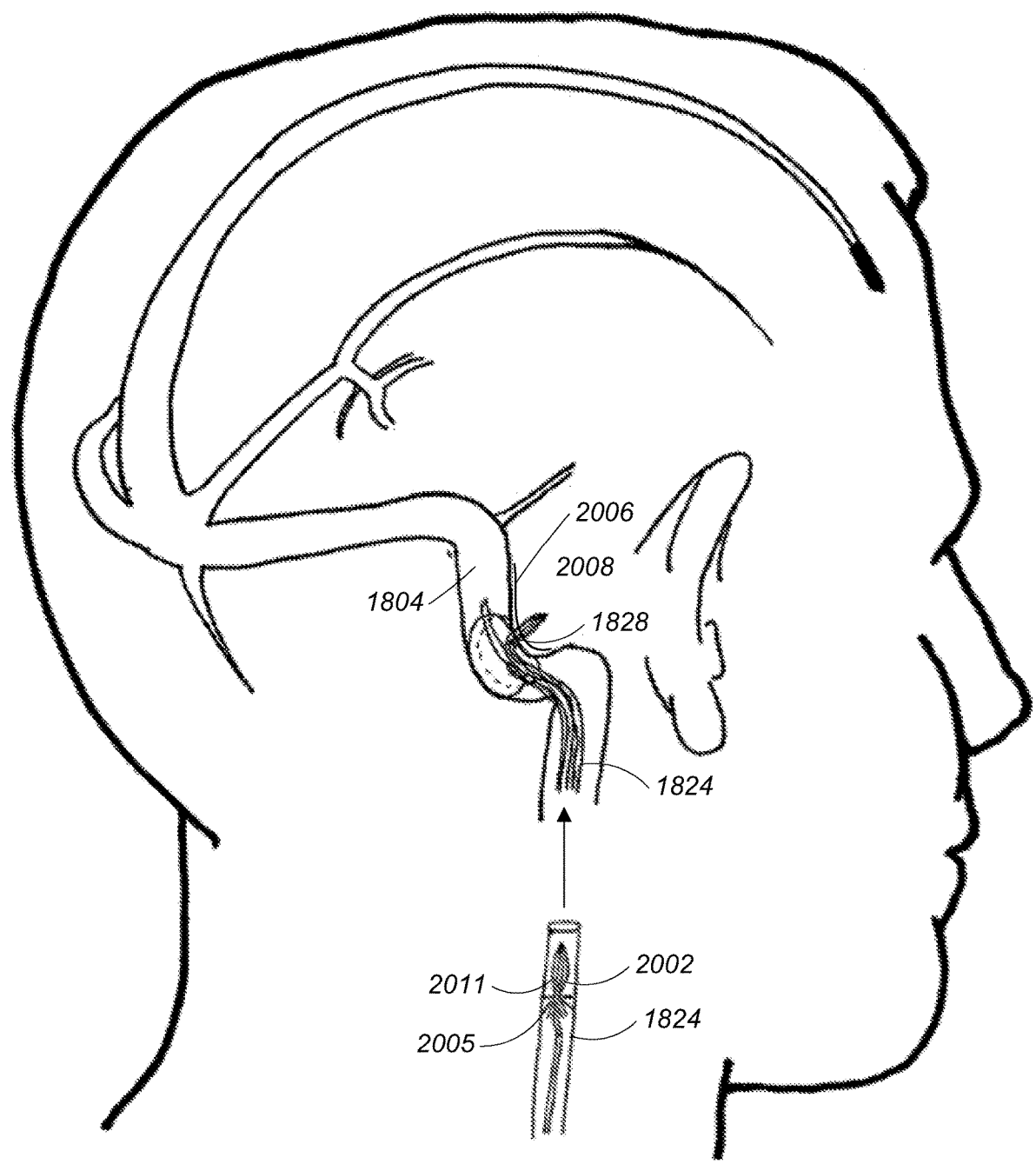
FIG. 20 shows a schematic of an endovascular cerebrospinal fluid shunt being implanted through the catheterization apparatus.

Referring to FIG. 20, with the opening 1828 of the delivery catheter 1824 positioned against the inner surface of the patient's sigmoid sinus 1804, an eCSFS device 2002 is threaded through the delivery catheter 1824, through the opening 1828 of the delivery catheter 1824, and penetrates through the wall of the sigmoid sinus 1803 through the arachnoid layer 2006, and into the subarachnoid space 2008. Upon emerging from the delivery catheter 1824 through the opening 1828, the filaments 2011 of the eCSFS device 2002 (a globe-type eCSFS device in this case) are allowed to return to their original, predefined globe-like shape, pushing against the brain parenchyma. Similarly, upon emerging from the delivery catheter 1824, the radial struts 2005 return to their original, predefined radially extending shape, pinching the sigmoid sinus wall between the radial struts 2005 and the globe-like assembly.

Figure 21:
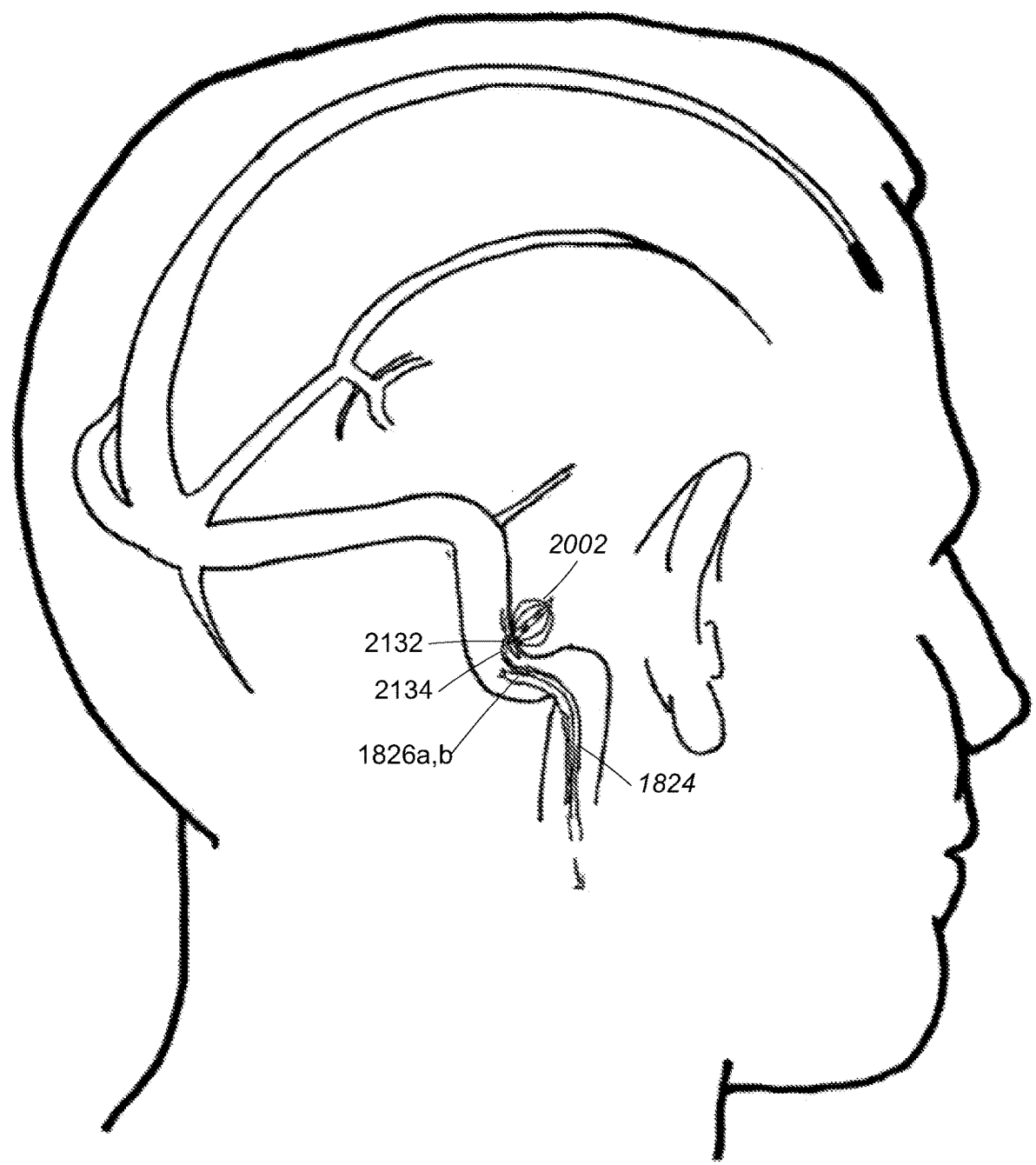
FIG. 21 shows the catheterization apparatus after shunt implantation with deflation of the balloon and expansion of the globe in the subarachnoid space.

Referring to FIG. 21, with the eCSFS device 2002 implanted, a surgeon can confirm that the eCSFS device 2002 is working by aspirating cerebrospinal fluid through a drainage tube 2134 that is within the delivery catheter 1824 and attached to the eCSFS device 2002. Once the eCSFS device 2002 is confirmed as working, the stabilization balloons 1826a, 1826b are deflated and the drainage tube 2134 is detached (e.g., by electrolytic detachment) at a detachment point 2132.

Figure 22:
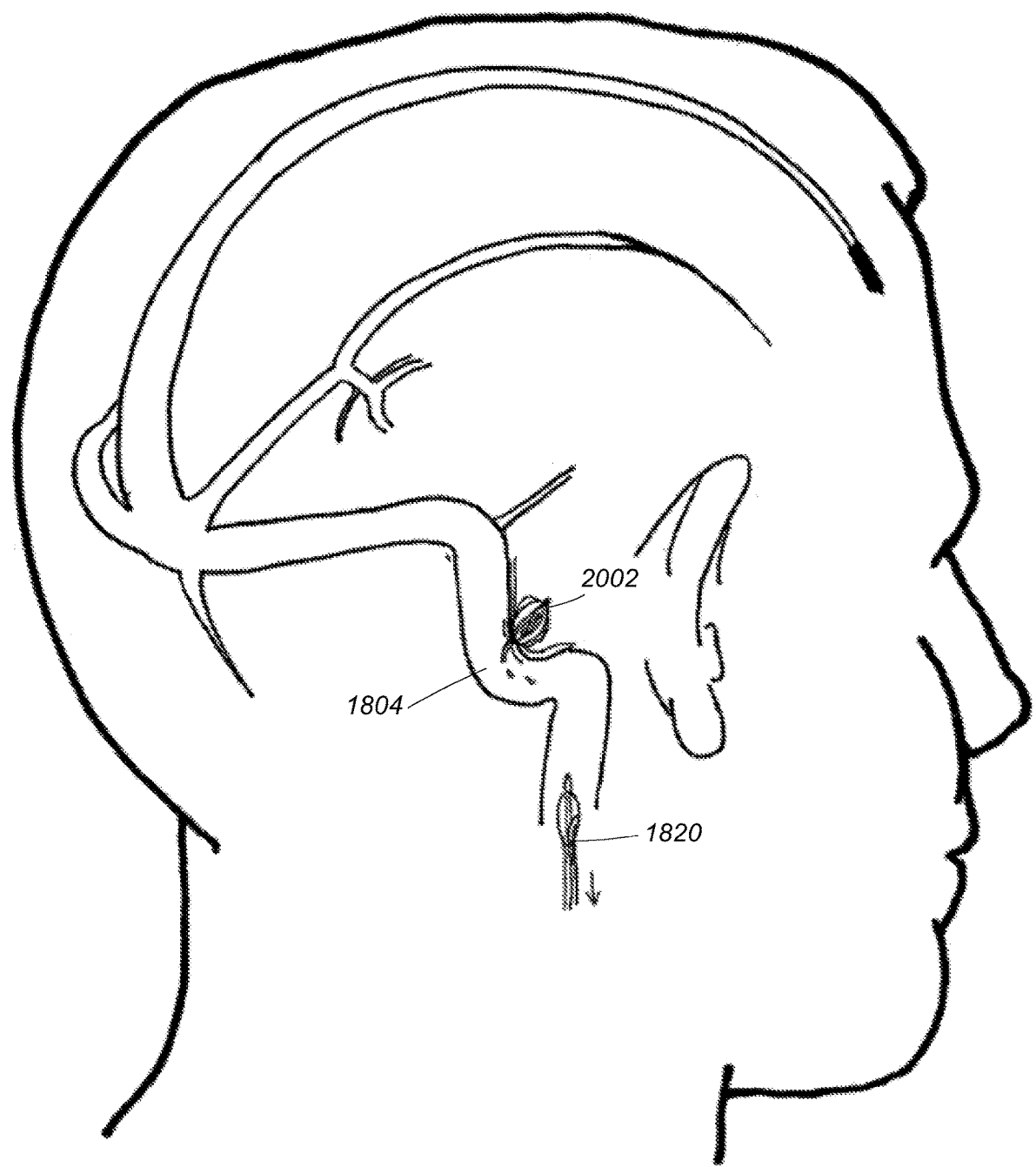
FIG. 22 shows the catheterization apparatus being withdrawn from the patient's sigmoid sinus.

Referring to FIG. 22, with the eCSFS device 2002 implanted and functioning in the sigmoid sinus 1804, the catheterization apparatus 1820 is withdrawn, completing the eCSFS implantation procedure.

Figure 23:
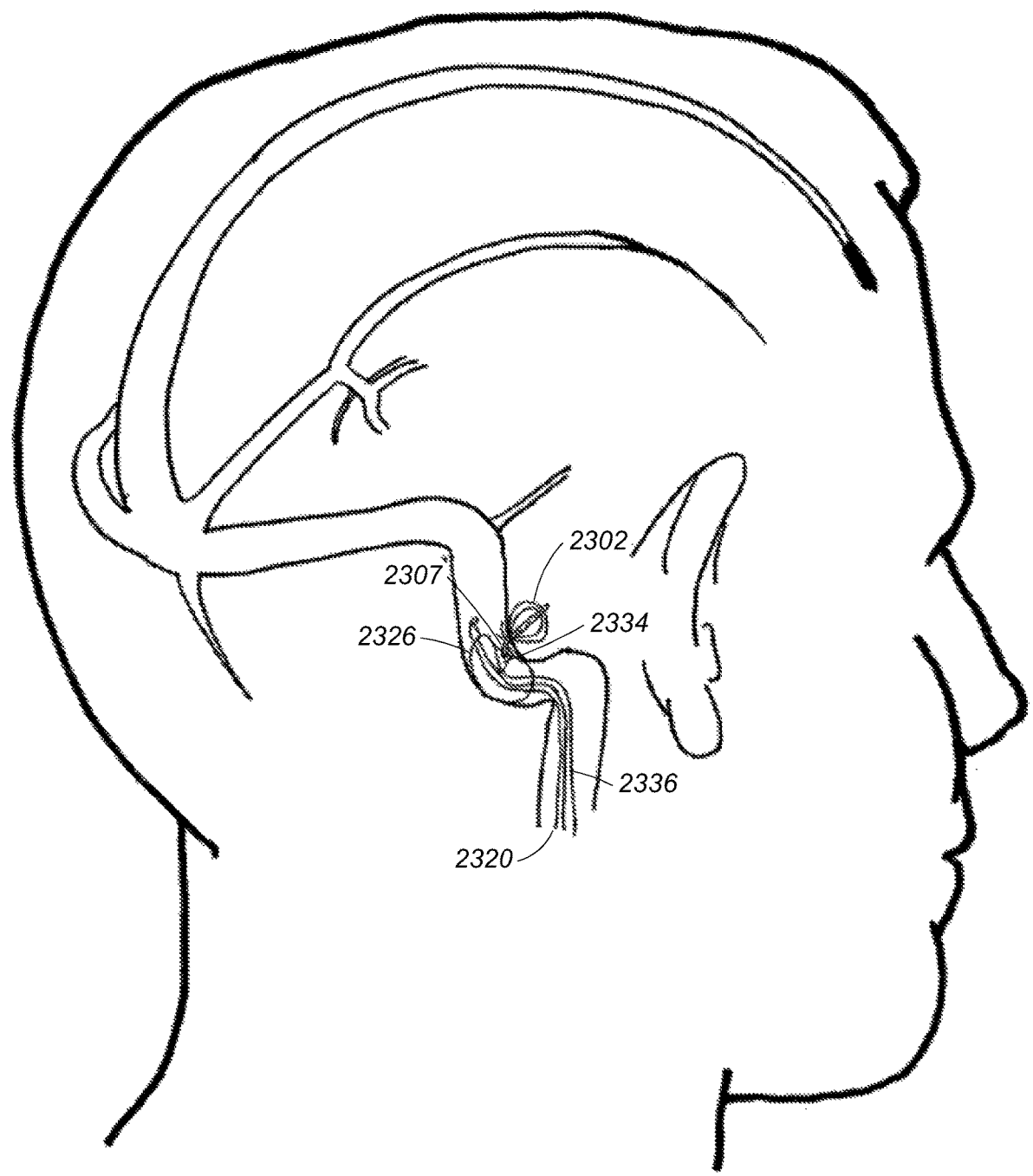
FIG. 23 shows a catheterization apparatus for patency testing.

Referring to FIG. 23, in some examples, it is necessary to test the patency (i.e., the openness) of a previously implanted eCSFS device 2302. In one example, to do so, a catheterization apparatus 2320 has a female receptacle 2334 mounted on one or more of the stabilization balloons 2326 and attached to a drainage catheter 2336 of the catheterization apparatus 2320. The catheterization apparatus 2320 is navigated to the site of the eCSFS device 2302 and the female receptacle 2334 is sealingly placed over the drainage tube 2307 of the eCSFS device 2302. A surgeon then attempts to draw cerebrospinal fluid through the eCSFS device and into the drainage catheter 2336. If cerebrospinal fluid is successfully drawn through the eCSFS device 2302, then the eCSFS device 2302 is open. Otherwise, the eCSFS device 2302 is occluded.

In some examples, the eCSFS device includes a radiopaque material that aids in guiding the catheterization apparatus 2320 to the delivery location and placing the female receptacle 2334 over the drainage tube 2307 of the eCSFS device 2302.

In some examples, the catheterization apparatus includes a steerable component in order to maintain the working port of the guide catheter in direction parallel to with the intracranial surface of the sigmoid sinus. In some examples, in order to evaluate a proximity of the eCSFS device to the sigmoid sinus wall and to evaluate the dural and arachnoid layers separating the device from the cerebrospinal fluid, the catheterization apparatus includes a phased array ultrasound micro catheter. In other examples, in order to evaluate a proximity of the eCSFS device to the sigmoid sinus wall and to evaluate the dural and arachnoid layers separating the device from the cerebrospinal fluid, the catheterization apparatus includes an OCT (optical coherence tomography) micro catheter imaging device.

In some examples, the opening at the end of the delivery catheter of the catheterization apparatus is specially configured to dock with the stent mounted ports described above. In some examples, rather than using stabilization balloons, the catheterization apparatus may include a temporary stent for stabilizing the delivery catheter and positioning the opening of the delivery catheter against the wall of the sigmoid sinus.

In some examples, rather than including two separate stabilization balloons, the catheterization apparatus includes a single stabilization balloon with an asymmetric shape such that the delivery catheter can easily be pushed against a wall of the sigmoid sinus in an area over the puncture site.

5. General Considerations for eCSFS and Deployment Devices

Exemplary dimensions for endovascular CSF shunt (eCSFS) device embodiments of the present disclosure are described herein. eCSFS devices should be dimensioned and configured to eliminate or minimize any disruption to sinus blood flow and occlusion within the sinus lumen. The aforementioned eCSFS deployment sites have been selected with this consideration in mind. That is, the dural venous sinuses described in this application (i.e., sigmoid, transverse, straight, or sagittal sinus) can have a relatively large diameter (e.g., 7 mm, 8 mm, 9 mm or more) compared to other dural venous sinuses. The increased sinus diameter accommodates eCSFS devices as described herein, while minimizing the impact of deployment procedures and a deployed device on venous blood flow within the sinus. A specialized catheterization apparatus has also been disclosed, which minimizes sinus occlusion during eCSFS deployment to preserve venous drainage of cerebral tissue.

The subarachnoid portions of the eCSFS device embodiments disclosed herein can include a shielding mechanism that protects the surface of the eCSFS, and in particular any openings in the surface of the eCSFS device that are designed to enable the passage or flow of CSF therethrough, from surrounding brain parenchyma (e.g., cerebellum) with a stent-like, umbrella-type, or equivalent configuration. The shielding mechanisms enable continuous CSF flow through the eCSFS device and mitigate clogging by structurally separating brain parenchyma tissue from the portions of the shunt device that are implanted into the subarachnoid space. These shielding mechanisms are particularly important if an eCSFS device is not deployed in a well-established subarachnoid cistern or where there is little or no CSF-filled space between the arachnoid layer and the pia. For example, in patients younger than 80 years old, the subarachnoid space accessible from the sigmoid sinus can include little or no CSF-filled space (e.g., 0-1 mm between arachnoid and pia) to accommodate the subarachnoid portion of an eCSFS device. The shielding aspects of the eCSFS devices address this challenge by advantageously creating, augmenting, and/or maintaining a subarachnoid cistern for eCSFS devices in such patients.

OTHER EMBODIMENTS

A number of embodiments have been described. Nevertheless, it will be understood that various modifications may be made without departing from the spirit and scope of the disclosure. Accordingly, other embodiments are within the scope of the following claims.

The invention claimed is:

1. An apparatus comprising
  a shunt for draining cerebrospinal fluid from a subarachnoid space of a patient, said shunt being an endovascularly implantable shunt having opposed first and second ends, said first end being constructed to pass through a wall of a dural venous sinus of said patient,
  a hollow passageway extending between said second end and said first end such that cerebrospinal fluid can be drained through said second end and into a location in a venous system of the patient, and
  a shielding mechanism coupled to said shunt, said shielding mechanism being and sized and configured to shield a portion of said shunt from surrounding brain parenchyma tissue within said subarachnoid space.

2. The apparatus of claim 1, wherein said shielding mechanism includes an umbrella-shaped member configured to be positioned within said subarachnoid space.

3. The apparatus of claim 1, wherein said shielding member comprises a screen configured to be positioned within said subarachnoid space.

4. The apparatus of claim 1, wherein said shielding mechanism is configured to transition into a predefined shape for deployment into said subarachnoid space from a collapsed state in which said shielding mechanism is loaded into a delivery catheter that is endovascularly guided to a desired location and passed through a wall of said dural venous sinus and into said subarachnoid space.

5. The apparatus of claim 1, wherein said shielding mechanism is configured to be mechanically opened by a surgeon operating a delivery catheter in which said shielding mechanism has been loaded while in a collapsed shape thereof, wherein mechanically opening said shielding mechanism causes deployment of said shielding mechanism within said subarachnoid space following endovascular delivery thereof.

6. The apparatus of claim 1, wherein said shielding mechanism comprises nickel and titanium.

7. The apparatus of claim 1, wherein said shielding mechanism is configured to automatically revert to a deployment shape.

8. The apparatus of claim 1, wherein said shielding mechanism comprises multiple filaments that cooperate to inhibit brain parenchyma from occluding said hollow passageway.

9. The apparatus of claim 1, wherein the second end further comprises a drainage tube that is connected to said first end, wherein, following delivery of said shunt, said drainage tube extends into or along an internal jugular vein of said patient.

10. The apparatus of claim 1, wherein the second end further comprises a drainage tube that is connected to said first end, wherein, following delivery of said shunt, said drainage tube extends along a blood vessel of said patient and is separated from a wall of said blood vessel by a distance that is sufficient to prevent incorporation of said drainage tube into said wall.

11. The apparatus of claim 1, wherein the second end further comprises a drainage tube that is connected to said first end, wherein, following delivery of said shunt, said drainage tube extends sufficiently to reach a superior vena cava and a right atrial junction of said patient.

12. The apparatus of claim 1, wherein said shunt is a first of a plurality of shunts, all of which are implanted in a dural venous sinus adjacent to each other.

13. The apparatus of claim 1, wherein said shunt is coated with heparin.

14. The apparatus of claim 1, further comprising balloon and a catheter having a distal end coupled to said balloon, said catheter having a lumen, wherein said shunt is disposed within said lumen and wherein said balloon transitions into an expanded state to partially occlude said dural venous sinus, thereby suppressing flow of blood through said dural venous sinus.

15. The apparatus of claim 1, further comprising an asymmetric balloon, wherein said shunt is disposed within a catheter having said asymmetric balloon disposed at a distal end thereof, wherein inflation of said asymmetric balloon stabilization drives said catheter away from being centered in a blood vessel during endoscopic delivery of said shunt.

16. The apparatus of claim 1, wherein said shunt comprises a drainage tube, said apparatus further comprising a drainage catheter and a receptacle coupled to said drainage catheter, wherein said receptacle is connected to said drainage tube of said shunt.

17. An apparatus comprising:
a shunt for draining cerebrospinal fluid from a subarachnoid space of a patient, said shunt being an endovascularly implantable shunt having opposed first and second ends,
a hollow passageway extending between said second end and said first end such that cerebrospinal fluid can be drained through said second end and into a location in a venous system of the patient, and
a shielding mechanism coupled to said shunt, said shielding mechanism being and sized and configured to shield a portion of said shunt from surrounding brain parenchyma tissue within said subarachnoid space.

18. The apparatus of claim 17, wherein said shielding mechanism is configured to transition into a predefined shape for deployment into said subarachnoid space from a collapsed state in which said shielding mechanism is loaded into a delivery catheter that is endovascularly guided to a desired location and passed through a wall of said dural venous sinus and into said subarachnoid space.

19. The apparatus of claim 17, wherein the second end further comprises a drainage tube that is connected to said first end, wherein, following delivery of said shunt, said drainage tube extends into or along an internal jugular vein of said patient.

20. A method comprising accessing a dural venous sinus in a patient, creating an opening between said dural venous sinus and a subarachnoid space of said patient, causing a first end of a shunt to enter said subarachnoid space while a second of said shunt remains in a location in a venous system of the patient, deploying a shielding member around said first end of said shunt, whereby cerebrospinal fluid drains from said subarachnoid space and into the venous system.

* * * * *